US009234222B2

(12) United States Patent
Van Den Berg et al.

(10) Patent No.: US 9,234,222 B2
(45) Date of Patent: Jan. 12, 2016

(54) MICROBIAL STRAINS PRODUCING SPHINGOID BASES OR DERIVATIVES THEREOF

(75) Inventors: Marco Alexander Van Den Berg, Poeldijk (NL); Steffen Schaffer, Herten (DE)

(73) Assignee: EVONIK DEGUSSA GMBH, Essen (DE)

(*) Notice: Subject to any disclaimer, the term of this patent is extended or adjusted under 35 U.S.C. 154(b) by 2135 days.

(21) Appl. No.: 11/666,863

(22) PCT Filed: Nov. 7, 2005

(86) PCT No.: PCT/EP2005/055791
§ 371 (c)(1),
(2), (4) Date: Jul. 24, 2007

(87) PCT Pub. No.: WO2006/048458
PCT Pub. Date: May 11, 2006

(65) Prior Publication Data
US 2008/0299625 A1    Dec. 4, 2008

(30) Foreign Application Priority Data
Nov. 5, 2004 (EP) .................................... 04105550

(51) Int. Cl.
C12P 13/00 (2006.01)
C12P 13/02 (2006.01)

(52) U.S. Cl.
CPC .............. C12P 13/001 (2013.01); C12P 13/02 (2013.01)

(58) Field of Classification Search
CPC ...... A61K 31/133; A61K 31/688; A61K 8/68
USPC ........................................................ 435/243
See application file for complete search history.

(56) References Cited

FOREIGN PATENT DOCUMENTS

| FR | 2843589 | * | 2/2004 | ............ C07C 215/24 |
| WO | WO 95/12683 | | 5/1995 | |

(Continued)

OTHER PUBLICATIONS

FR 2843589 A1 (L'OREAL SA[OREA]) Aug. 13, 2002 (abstract)
World Patents Index [online]. London, UK: Derwent Publications, Ltd. [retrieved on Jul. 31, 2010], Accession No. 2004-241470.*

(Continued)

*Primary Examiner* — Sharmila G. Landau
*Assistant Examiner* — Sheridan Macauley
(74) *Attorney, Agent, or Firm* — Oliff PLC

(57) ABSTRACT

The present invention provides microbial strains, in particular yeast strains, that produce at least 0.1 mg per g biomass dry weight of a sphingoid base. The present invention further provides a method to obtain sphingoid base-producing microbial strains comprising incubating a population of microbial cells in the presence of a suitable concentration of a toxin, selecting cells that are resistant against said toxin, and isolating cells out of the toxin-resistant cell population that produce at least 0.1 mg per g biomass dry weight of the sphingoid base of Formula I. Optionally, the method further comprises subjecting a population of toxin-resistant microbial cells that produce at least 0.1 mg per g biomass dry weight of the sphingoid base of Formula I to DNA-mediated transformation with a polynucleotide encoding an enzyme of the sphingolipid metabolic pathway. The present invention further provides a polypeptide having dihydroceramide desaturase activity obtainable form *Pichia ciferrii*.

4 Claims, 7 Drawing Sheets

Figure 1A

(56) References Cited

FOREIGN PATENT DOCUMENTS

WO    WO 99/57279 A1    11/1999
WO    WO 00/01839 A1    1/2000

OTHER PUBLICATIONS

International Preliminary Report on Patentability for PCT/EP2005/055791, Nov. 7, 2005, Patent Cooperation Treaty International Search Authority, pp. 1-9.*

Barenholz, Y. et al., "Identification of the Enzymatic Lesions Responsible for the Accumulation of Acetylated Sphingosine Bases in the Yeast Hansenula ciferri," Biochimica and Biophysica Acta, vol. 306, No. 2, pp. 341-345, 1973.

Grilley, M. M. et al., "Syringomycin Action Gene SYR2 is Essential for Spingolipid 4-Hydroxylation in Saccharomyces cerevisiae, *," The Journal of Biological Chemistry, vol. 273, No. 18, pp. 11062-11068, 1998.

Bae et al., "Cloning and Functional Characterization of the SUR2/SYR2 Gene Encoding Sphinganine Hydroxylase in Pichia Ciferrii," Yeast, vol. 21, pp. 437-443, Apr. 15, 2004.

"Delta 4-(E)-Sphingolipid Desaturase," XP 002326875, Oct. 25, 2007.

"Pichia Pastoris Delta 4-(E)-Spingolipid Desturase (DES) Gene, Complete Cds," XP002326876, Sep. 6, 2004.

Sperling, P. et al., "Plant Spingolipids: Structural Diverity, Biosynthesis, First Genes and Functions," Biochimica and Biophysica Acta, vol. 1632, No. 1-3, pp. 1-15, Jun. 10, 2003.

Chung, N. et al., "Phytosphingosine As a Specific Inhibitor of Growth and Nutrient Import in Saccharomyces cerevisiae*," The Journal of Biological Chemistry, vol. 273, No. 38, pp. 35614-35621, Sep. 21, 2001.

Abbas et al., "Fumonisin- and AAL-Toxin-Induced Disruption of Sphingolipid Metabolism With Accumulation of Free Sphingoid Bases[1]," Plant Physio., vol. 106, pp. 1085-1093, 1994.

Feb. 5, 2010 English Translation of Chinese Office Action issued in corresponding Chinese Patent Application No. 200580045976.X.

Kaneshiro et al., "Fumonisin-Stimulated N-Acetyldihydrosphingosine, N-Acetylphytosphingosine, and Phytosphingosine Products of Pichia (Hansenula) ciferri, NRRL Y-1031," Current Microbiology, vol. 24, pp. 391-234, 1992.

Feb. 3, 2010 European Office Action issued in corresponding European Application No. 05 811 034.7.

Jun. 14, 2011 English-language translation of Notice of Reasons for Rejection issued in Japanese Application No. 2007-539587.

* cited by examiner

```
SEQUENCE LISTING

<160> NUMBER OF SEQ ID NOS: 30

<210> SEQ ID NO 1
<211> LENGTH: 351
<212> TYPE: PRT
<213> ORGANISM: Pichia ciferrii

<400> SEQUENCE: 1

Met Ala Thr Ile Thr His Arg Lys Asn Pro Ser Gln Pro Ile Thr Phe
1               5                   10                  15

Gln Thr Pro Pro Ala Asp Ala Pro Ile Glu Lys Leu Asn Asp Phe Tyr
            20                  25                  30

Trp Thr Asn Glu Thr Glu Pro His Thr Ile Arg Arg Lys Leu Ile Leu
        35                  40                  45

Lys Lys Tyr Pro Lys Ile Thr Glu Leu Cys Gly Pro Glu Pro Leu Thr
    50                  55                  60

Lys Tyr Ile Ile Phe Gly Val Val Ser Leu Gln Leu Ser Ile Ala Tyr
65                  70                  75                  80

Tyr Leu Arg Asn Thr Pro Phe Leu Ser Trp Lys Phe Phe Leu Leu Ser
                85                  90                  95

Tyr Ile Ile Gly Ala Thr Ala Asn Gln Asn Val Phe Leu Ala Ile His
            100                 105                 110

Glu Leu Thr His Asn Leu Ala Phe Lys Lys Pro Leu His Asn Lys Leu
        115                 120                 125

Tyr Ala Ile Phe Thr Asn Ile Pro Ile Gly Ile Pro Tyr Ser Ala Ser
    130                 135                 140

Phe Gln Pro Tyr His Gln Leu His His Lys Tyr Leu Gly Asp Glu Val
145                 150                 155                 160
```

| Leu | Asp | Thr | Asp | Val | Pro | Thr | Lys | Tyr | Glu | Ala | Ile | Val | Leu | Ser | Asn |
|---|---|---|---|---|---|---|---|---|---|---|---|---|---|---|---|
| | | | | 165 | | | | | 170 | | | | | 175 | |

Val Leu Gly Lys Ser Phe Phe Ala Thr Phe Gln Ile Leu Phe Tyr Ala
            180                 185                 190

Leu Arg Pro Met Phe Ile Thr Gln Ile Lys Phe Thr Tyr Ile His Leu
        195                 200                 205

Leu Asn Val Leu Val Gln Leu Phe Val Asp Phe Leu Ile Val Lys Tyr
    210                 215                 220

Trp Gly Trp Lys Ser Leu Ser Tyr Phe Ile Phe Ser Ser Phe Leu Ala
225                 230                 235                 240

Gly Ser Leu His Pro Cys Ser Gly His Phe Ile Ala Glu His Tyr Ile
                245                 250                 255

Met Asp Pro Pro Lys Thr Tyr Asn Arg Tyr Lys Asp His Pro Pro Leu
            260                 265                 270

Glu Thr Tyr Ser Tyr Tyr Gly Ala Leu Asn Leu Val Thr Trp Asn Val
        275                 280                 285

Gly Leu His Asn Glu His His Asp Phe Pro Tyr Val Ala Trp Ser Lys
    290                 295                 300

Leu His Lys Leu Asn Glu Val Ala Asn Glu Phe Tyr Cys Asp Leu Pro
305                 310                 315                 320

Lys His Asp Ser Trp Thr Met Val Ile Val Asn Phe Ile Leu Asp Lys
                325                 330                 335

Asn Val Leu Leu Tyr Asn Arg Val Lys Arg Glu Thr Ala Lys Lys
            340                 345                 350

<210> SEQ ID NO 2
<211> LENGTH: 1056
<212> TYPE: DNA
<213> ORGANISM: Pichia ciferrii

<400> SEQUENCE: 2

```
atggctacaa ttacacatag aaaaaaccct tcacaaccaa taactttcca acacctcca      60
gcagatgctc caattgaaaa attaaatgat ttttattgga caaatgaaac tgaacctcat    120
acaattagaa gaaattaat attgaaaaaa tatccaaaaa ttacagaact tgtggaccct    180
gaacctttaa ctaaatatat tattttcgga gttgtttcat tacaattatc aattgcttat    240
tatttaagaa atactccatt tttaagttgg aaattctttt tgttaagtta tataattggt    300
gctactgcaa tcaaaatgt cttttagct attcatgaat taactcataa tttagcattt      360
aaaaaaccat tacataacaa attatatgca attttcacaa atattccaat tggtataccct    420
tattcagctt ctttccaacc ttatcatcaa ttacatcata atatttagg tgatgaagtt    480
ttagatactg atgtcccaac aaaatatgaa gctatagttt tatcaaatgt cttgggaaa    540
tcatttttg caactttcca aatcttattt tatgctttaa gaccaatgtt tattacacaa    600
attaaattta cttatattca tttacttaac gtcttggttc aactatttgt tgatttctta    660
attgtgaaat actggggttg gaaatcatta agttatttca tctttagttc attttttagct    720
ggttctttac atccatgttc aggtcatttc attgctgaac attatatcat ggatccacca    780
aagacttata cagatataa agatcatcca ccttagaaa cttattcata ttatggtgcc    840
ttaaatttag ttacatggaa tgttggtcta cataatgaac atcatgattt cccatatgtt    900
gcttggtcaa aacttcataa attgaatgaa gttgctaatg agtttattg tgatttacca    960
aaacatgatt catggactat ggttattgtt aacttcattc ttgataaaaa tgtcttatta  1020
tacaatagag ttaaaagaga aactgcaaag aaataa                              1056
```

<210> SEQ ID NO 3
<211> LENGTH: 2534
<212> TYPE: DNA
<213> ORGANISM: Pichia ciferrii

<400> SEQUENCE: 3

| | |
|---|---|
| catatggtat tattctaatt atacatagac aagtgttacc acaagtttct catgataaat | 60 |
| ggaaagtatt tggattatgg actttagtta acgcatttgc tgttggttat catccgattc | 120 |
| aaaatacttg gttacaacta aactgtgatt ctccacagga aagaagtatt tcaattgcac | 180 |
| tttgggtaat gtttgccatg attggactaa tgagtggatc tcagttgttt agacaagatg | 240 |
| ataaaccttt atatcaaaag gaactttag ccatgatttg tatggttttt ggaggattcc | 300 |
| tcatatcctt gggacagtat tcttatact atcatctaaa caggaaaaag caatcaaatg | 360 |
| agcgtaaatg ctattataa atgatatttt gactcattaa tttgtgaata ttttgtagtt | 420 |
| tatactgatt acataaccat gacataagca atcaggaaac gtttttttttt ttattttat | 480 |
| ttttattttt acttttgcga atcgcctcgt ttaaaacgtt taaaaaacca aaatttaat | 540 |
| tgttttctat taacatcagc tcatttttaat tgtatttaaa gaacagctca acttttttctt | 600 |
| tgaaggaag atcagactac aaatttgtca actccaaaaa ctcctattta tacacagaga | 660 |
| aattctttttt tctctttttc cattcattta taccccctaat atcattggat ctcaaaaaag | 720 |
| ttgttattcg agatctgaat ctggatctat attatattaa taaaaagatt ccaaaagctc | 780 |
| atcatggcta caattacaca tagaaaaaac ccttcacaac caataacttt ccaaacaccct | 840 |
| ccagcagatg ctccaattga aaaattaaat gattttttatt ggacaaatga aactgaaccct | 900 |
| catacaatta aagaaaatt aatattgaaa aaatatccaa aaattacaga actttgtgga | 960 |
| cctgaacctt taactaaata tattattttc ggagttgttt cattacaatt atcaattgct | 1020 |
| tattattttaa gaaatactcc attttttaagt tggaaattct ttttgttaag ttatataatt | 1080 |
| ggtgctactg caaatcaaaa tgtctttttta gctattcatg aattaactca taatttagca | 1140 |
| tttaaaaaac cattacataa caattatat gcaattttca caaatattcc aattggtata | 1200 |
| ccttattcag cttctttcca accttatcat caattacatc ataaatatt aggtgatgaa | 1260 |
| gttttagata ctgatgtccc aacaaaatat gaagctatag ttttatcaaa tgtcttgggg | 1320 |
| aaatcatttt ttgcaacttt ccaaatctta ttttatgctt taagaccaat gtttattaca | 1380 |
| caaattaaat ttacttatat tcatttactt aacgtcttgg ttcaactatt tgttgatttc | 1440 |
| ttaattgtga atactggggg ttggaaatca ttaagttatt tcatctttag ttcattttta | 1500 |
| gctggttctt tacatccatg ttcaggtcat ttcattgctg aacattatat catggatcca | 1560 |
| ccaaagactt ataacagata taagatcat ccacctttag aaacttattc atattatggt | 1620 |
| gccttaaatt tagttacatg gaatgttggt ctacataatg aacatcatga tttcccatat | 1680 |
| gttgcttggt caaaacttca taattgaat gaagttgcta atgagttta ttgtgattta | 1740 |
| ccaaaacatg attcatggac tatggttatt gttaacttca ttcttgataa aaatgtctta | 1800 |
| ttatacaata gagttaaaag agaaactgca agaaataaa atccataaaa ttatcattat | 1860 |
| ttataaacta tatatgtacg aattgggctg gagaatagag gtataacaaa atatacaaaa | 1920 |
| catatcatta tttatacgaa aattgtagtc accagatagt catctaaaat gctgacatgt | 1980 |
| aactgtcgtc gtattcgttc aatttgatgt gaagtatcca tgctcaatgc tgagatcctc | 2040 |
| atacaaaaaa taattagcga aaagcaaaaa ataaaaaaaa aaaaaaccct ttaatctcct | 2100 |

-continued

```
gataatttaa ctaacaaatt ttgtcaaacg gtagaaacga ttcgaacttt atcaattcta    2160
gttttgaaca agatcagttg tcacaaaaga acgaagtgtt aaacgataaa tcattgattg    2220
tcaattgtat ataaacacag acaggaaacc gttgaattcg ttgtatcttt atcaaaactt    2280
aatcattaat actcaagtac aatagaattg acaatatgcc tttcactgat caaacatcac    2340
caaatgcccc aattagggaa aagatggaag ctttaatccg tcaaaacaa caagaaatca     2400 ctaaaggtct tgaagcttta gaaccaactg ctagattctt tgctgattct tggtctcgtg    2460
gtgaaagtgc tggaggtggt acttcatgtg ttattcaaga tggtgaagtt tttgaaaaag    2520
gtggtgtgaa tatt                                                     2534
```

<210> SEQ ID NO 4
<211> LENGTH: 23
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t

<400> SEQUENCE: 4

```
acwttycaaa thttnttyta ygc                                              23
```

<210> SEQ ID NO 5
<211> LENGTH: 23
<212> TYPE: DNA
<213> ORGANISM: Artificial sequence
<220> FEATURE:
<223> OTHER INFORMATION: primer

<400> SEQUENCE: 5

```
ggraaatcat gatgytcrtt atg                                              23
```

<210> SEQ ID NO 6
<211> LENGTH: 29
<212> TYPE: DNA
<213> ORGANISM: Artificial sequence
<220> FEATURE:
<223> OTHER INFORMATION: primer

<400> SEQUENCE: 6

```
aaagatcatc cacctttaga aacttattc                                        29
```

<210> SEQ ID NO 7
<211> LENGTH: 27
<212> TYPE: DNA
<213> ORGANISM: Artificial sequence
<220> FEATURE:
<223> OTHER INFORMATION: primer

<400> SEQUENCE: 7

```
gacctgaaca tggatgtaaa gaaccag                                          27
```

<210> SEQ ID NO 8
<211> LENGTH: 19
<212> TYPE: DNA
<213> ORGANISM: Artificial sequence
<220> FEATURE:
<223> OTHER INFORMATION: primer

<400> SEQUENCE: 8

```
tttttacttt tgcgaatcg                                                   19
```

<210> SEQ ID NO 9
<211> LENGTH: 29
<212> TYPE: DNA
<213> ORGANISM: Artificial sequence
<220> FEATURE:
<223> OTHER INFORMATION: primer

<400> SEQUENCE: 9
aaagatcatc cacctttaga aacttattc            29

<210> SEQ ID NO 10
<211> LENGTH: 24
<212> TYPE: DNA
<213> ORGANISM: Artificial sequence
<220> FEATURE:
<223> OTHER INFORMATION: primer

<400> SEQUENCE: 10
ctgttataag tctttggtgg atcc            24

<210> SEQ ID NO 11
<211> LENGTH: 36
<212> TYPE: DNA
<213> ORGANISM: Artificial sequence
<220> FEATURE:
<223> OTHER INFORMATION: primer

<400> SEQUENCE: 11
tatatacata tggctagatt gacagaagtc gatcag            36

<210> SEQ ID NO 12
<211> LENGTH: 46
<212> TYPE: DNA
<213> ORGANISM: Artificial sequence
<220> FEATURE:
<223> OTHER INFORMATION: primer

<400> SEQUENCE: 12
cccatccact aagtttaaac acccatacaa aatcgagctt caaatc            46

<210> SEQ ID NO 13
<211> LENGTH: 39
<212> TYPE: DNA
<213> ORGANISM: Artificial sequence
<220> FEATURE:
<223> OTHER INFORMATION: primer

<400> SEQUENCE: 13
tatatacata tgctaatcac aacagaacat tctctaacg            39

<210> SEQ ID NO 14
<211> LENGTH: 45
<212> TYPE: DNA
<213> ORGANISM: Artificial sequence
<220> FEATURE:
<223> OTHER INFORMATION: primer

<400> SEQUENCE: 14
tgtttaaact tagtggatgg gaaaccctgt agaactggga caaac            45

<210> SEQ ID NO 15
<211> LENGTH: 39
<212> TYPE: DNA
<213> ORGANISM: Artificial sequence
<220> FEATURE:

```
<223> OTHER INFORMATION: primer

<400> SEQUENCE: 15
tatatacata tgctaatcac aacagaacat tctctaacg                                39

<210> SEQ ID NO 16
<211> LENGTH: 36
<212> TYPE: DNA
<213> ORGANISM: Artificial sequence
<220> FEATURE:
<223> OTHER INFORMATION: primer

<400> SEQUENCE: 16
tatatacata tggctagatt gacagaagtc gatcag                                   36

<210> SEQ ID NO 17
<211> LENGTH: 87
<212> TYPE: DNA
<213> ORGANISM: Artificial sequence
<220> FEATURE:
<223> OTHER INFORMATION: primer

<400> SEQUENCE: 17
tagaagttcc agaaactact ttccaaactt caaatcaac tttattatca atggctacaa          60
ttacacatag aaaaaaccct tcacaac                                             87

<210> SEQ ID NO 18
<211> LENGTH: 50
<212> TYPE: DNA
<213> ORGANISM: Artificial sequence
<220> FEATURE:
<223> OTHER INFORMATION: primer

<400> SEQUENCE: 18
tatactgcag gcatattgtc aattctattg tacttgagta ttaatgatta                    50

<210> SEQ ID NO 19
<211> LENGTH: 39
<212> TYPE: DNA
<213> ORGANISM: Artificial sequence
<220> FEATURE:
<223> OTHER INFORMATION: primer

<400> SEQUENCE: 19
tatactgcag tgtgctctaa atttgcccgg ttcgcgacg                                39

<210> SEQ ID NO 20
<211> LENGTH: 50
<212> TYPE: DNA
<213> ORGANISM: Artificial sequence
<220> FEATURE:
<223> OTHER INFORMATION: primer

<400> SEQUENCE: 20
tgataataaa gttgattttg aagtttggaa agtagtttct ggaacttcta                    50

<210> SEQ ID NO 21
<211> LENGTH: 39
<212> TYPE: DNA
<213> ORGANISM: Artificial sequence
<220> FEATURE:
<223> OTHER INFORMATION: primer

<400> SEQUENCE: 21
tatactgcag tgtgctctaa atttgcccgg ttcgcgacg                                39
```

```
<210> SEQ ID NO 22
<211> LENGTH: 50
<212> TYPE: DNA
<213> ORGANISM: Artificial sequence
<220> FEATURE:
<223> OTHER INFORMATION: primer

<400> SEQUENCE: 22
tatactgcag gcatattgtc aattctattg tacttgagta ttaatgatta          50

<210> SEQ ID NO 23
<211> LENGTH: 32
<212> TYPE: DNA
<213> ORGANISM: Artificial sequence
<220> FEATURE:
<223> OTHER INFORMATION: primer

<400> SEQUENCE: 23
tatagtcgac gaattctctt aaatgatgtt gg                             32

<210> SEQ ID NO 24
<211> LENGTH: 49
<212> TYPE: DNA
<213> ORGANISM: Artificial sequence
<220> FEATURE:
<223> OTHER INFORMATION: primer

<400> SEQUENCE: 24
gttttagctt ttttatggaa aacttgtttg gtttgaccac cgtaaccgg           49

<210> SEQ ID NO 25
<211> LENGTH: 70
<212> TYPE: DNA
<213> ORGANISM: Artificial sequence
<220> FEATURE:
<223> OTHER INFORMATION: primer

<400> SEQUENCE: 25
ccggttacgg tggtcaaacc aaacaagttt tccataaaaa agctaaaact accaaaaaag    60
ttgttttacg                                                            70

<210> SEQ ID NO 26
<211> LENGTH: 32
<212> TYPE: DNA
<213> ORGANISM: Artificial sequence
<220> FEATURE:
<223> OTHER INFORMATION: primer

<400> SEQUENCE: 26
tatagagctc aattccaatg ttttgatctg tc                             32

<210> SEQ ID NO 27
<211> LENGTH: 32
<212> TYPE: DNA
<213> ORGANISM: Artificial sequence
<220> FEATURE:
<223> OTHER INFORMATION: primer

<400> SEQUENCE: 27
tatagtcgac gaattctctt aaatgatgtt gg                             32

<210> SEQ ID NO 28
<211> LENGTH: 32
<212> TYPE: DNA
```

```
<213> ORGANISM: Artificial sequence
<220> FEATURE:
<223> OTHER INFORMATION: primer

<400> SEQUENCE: 28
tatagagctc aattccaatg ttttgatctg tc                                    32

<210> SEQ ID NO 29
<211> LENGTH: 25
<212> TYPE: DNA
<213> ORGANISM: Artificial sequence
<220> FEATURE:
<223> OTHER INFORMATION: primer

<400> SEQUENCE: 29
ctaggaaaga tagggacaa tcaag                                             25

<210> SEQ ID NO 30
<211> LENGTH: 24
<212> TYPE: DNA
<213> ORGANISM: Artificial sequence
<220> FEATURE:
<223> OTHER INFORMATION: primer

<400> SEQUENCE: 30
aaggttcagg tccacaaagt tctg                                             24
```

MICROBIAL STRAINS PRODUCING SPHINGOID BASES OR DERIVATIVES THEREOF

The term "sphingolipids" refers to a group of lipids that are derived from sphingoid bases like sphingosine. Sphingolipids occur frequently in cellular membranes of animals, plants and microorganisms.

Ceramides are a specific group of sphingolipids containing sphingosine, phytosphingosine or dihydrosphingosine (sphinganine) as a base (sphingoid base) in amide linkage with a fatty acid. Ceramides are the main lipid component of the stratum corneum, the upper layer of the skin. Topical application of compositions comprising sphingolipids, such as ceramides, improves the barrier function and moisture-retaining properties of the skin (Curratolo, 1987, Pharm. Res. 4, 271-277; Kerscher et al., 1991, Eur. J. Dermatol. 1, 39-43). Furthermore, sphingoid bases as such are known to mediate several physiological effects as inhibiting the activity of protein kinase C and are therefore included in cosmetic or dermatological compositions for their anti-inflammatory and antimicrobial activity.

As sphingosine is the major sphingoid base component of sphingolipids in human, it is of considerable commercial interest to produce sphingosine and sphingosine-containing sphingolipids for food, pharmaceutical and cosmetic applications.

Currently, several routes for the chemical synthesis of sphingosine (and sphinganine) have been developed. However, due to the presence of two stereocenters in these molecules, chemical synthesis results in a racemic mixture with only 25% representing the naturally occurring stereochemical configuration. Moreover, extensive protection chemistry has to be applied due to the presence of three functional groups within these molecules. Consequently, sphingosine and sphinganine produced via chemical synthesis are extremely expensive not allowing for its incorporation into food and cosmetic formulations. This is also true for pure sphingosine and sphinganine isolated from natural sources, such as brain or chicken eggs. Heterogeneous sphingolipids preparations, which have been extracted from animal sources, are also available. Though cheaper than the pure compounds, they suffer from compositional heterogeneity and are potentially unsafe as they might contain pathogenic agents.

Contrary to mammals, phytosphingosine and not sphingosine is the major sphingoid base component of sphingolipids in microorganisms. Usually, phytosphingosine does not accumulate in microorganisms, but is part of the de novo sphingolipid biosynthesis pathway. The yeast *Pichia ciferrii* (Wickerham and Stodola, 1960, J. Bacteriol. 80, 484-491) was shown to produce rather high levels of sphingoid bases and derivatives thereof, but exclusively phytosphingosines with C18-phytosphingosine and acetylated derivatives thereof as the main constituents. The production level was much higher than necessary for de novo sphingolipid biosynthesis. This phytosphingosine can be extracted from the yeast and chemically converted into e.g. ceramides, thereby obtaining pure cosmetic ingredients (see e.g. WO 93/20038).

WO 00/01839 discloses *Pichia ciferrii* strains obtained by classical mutagenesis showing an enhanced production level of the sphingoid base phytosphingosine.

However, an economically feasible way of producing the naturally occurring stereoisomers of sphingosine and sphinganine as pure compounds is not available and is extremely desirable.

Barenholz et al (1973, Biochimica et Biophysica Acta 306: 341-345) describe the conversion by cell-free extracts of minute amounts of radioactively labelled artificial substrates into dihydrosphingosine (sphinganine). However, the whole cells almost exclusively produce phytosphingosine, as reported by the authors on page 344: "This work measured only the synthesis of dihydrosphingosine, while the high producers accumulated mostly acetylated phytosphingosine". Sphinganine accumulating yeasts have been described by disturbing the function of the SYR2 gene in haploid *Saccharomyces cerevisiae* cells (Grilley et al., 1998, J Biol Chem 273:11062-11068) via screening for syringomycinE resistant mutants. However, these yeasts produce very low levels of sphinganine which are not enough for an efficient production.

Bae et al. (2004, Yeast, 21: 437-443) describe the sphinganine production level of a *Saccharomyces cerevisiae* sur2 null mutant lacking C4-sphinganine hydroxylase. It was shown to be only 346 pmol/mg protein, which corresponds to approximately 10 microgram/g biomass. This is far too low for a commercial process.

It is therefore an object of the present invention to provide microbial strains that are capable of producing sphingoid bases other than C-18 phytosphingosine, in particular sphinganine and/or sphingosine.

Therefore, in a first aspect, the present invention provides a microbial strain, in particular a yeast strain, that produces at least 0.1 mg per g biomass dry weight of a sphingoid base according to Formula I:

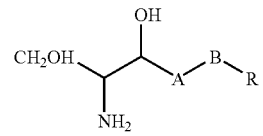

or a salt or ester thereof,
wherein A-B is selected from the group consisting of $CH_2$—$CH_2$ and $CH$=$CH$;
and wherein R is selected from the group consisting of:
  a) $(CH_2)_m$—X—$(CH_2)_n$—$CH_3$, wherein m and n each individually are between 0 and 18 (inclusive), and X is $CH_2$—$CH_2$, $CH$=$CH$, $C$≡$C$, $CHOH$—$CH_2$, $HC$=$O$—$CH_2$, with the proviso that m+n should be between 0 and 18 (inclusive), and
  b) $(CH_2)_p$—$CH$=$CH$—$(CH_2)_q$—$CH$=$CH$—$(CH_2)_w$—$CH_3$, wherein p, q and w each individually are between 0 and 16 (inclusive), with the proviso that p+q+w should be between 0 and 16 (inclusive).

Preferably, the yeast strain of the invention produces at least 1 mg per g biomass dry weight of a sphingoid base according to Formula I, more preferably at least 10 mg per g biomass dry weight. The skilled person will thereby understood that an upper limit in sphingoid base productivity may be around 500 mg per g biomass dry weight.

The sphingoid base productivity of the microbial strain of the invention is preferably measured when the sphingoid base-producing microbial strain is cultured under the following conditions. Microbial cells are inoculated from an agar plate in 100 ml YEPD medium in a 500 ml shake-flask and incubated for 72 hours at 30° C. and 280 rpm. Subsequently, 1% of this culture is transferred to a new 500 ml shake-flask with baffle filled with 100 ml LCBNB production medium and incubated for 96 hours at 30° C. and 280 rpm.

Sphingoid base productivity conveniently is measured by HPLC or MS.

The microbial strain of the invention preferably is a yeast strain, more preferably a strain of *Pichia*, most preferably a strain of *Pichia ciferrii*.

In another embodiment, the sphingoid base according to Formula I is in the form of an acyl ester. The acyl group may be attached to the sphingoid base via a hydroxyl group, i.e. a "real" ester linkage and/or via an amino group, i.e. an amide linkage. Preferably, the acyl group is a straight short-chain acyl group of 1-4 carbon atoms, more preferably an acetyl group.

In a preferred embodiment, the sphingoid base according to Formula I has the D-erythro-(2R,3S)-configuration according to Formula II:

$$CH_2OH \underset{NH_2}{\overset{OH}{-}} A-B-R$$

wherein A-B and R are as defined above.

Also preferred are compounds according to Formula I or II, wherein R is $(CH_2)_m$—X—$(CH_2)_n$—$CH_3$, wherein, more preferably, m is 0, X is $CH_2$—$CH_2$ or CHOH—$CH_2$, most preferably X is $CH_2$—$CH_2$, and n is between 8 and 12, most preferably n is 10. Especially preferred is a compound according to Formula I or II wherein A-B is $CH_2$—$CH_2$ or CH=CH and R is $(CH_2)_{12}$—$CH_3$.

The skilled person will appreciate that microbially produced sphingoid bases may constitute a mixture of sphingoid bases with different chain lengths, i.e. different lengths of the R-group. Sometimes, one chain length may predominantly be present, although mixtures comprising about equal amounts of different chain lengths are also possible.

In a second aspect, the present invention provides a method for the isolation of a microbial strain according to the first aspect.

The method comprises incubating a population of microbial cells in the presence of a suitable concentration of a toxin, selecting a subpopulation of cells that are resistant against said toxin, and isolating cells out of the toxin-resistant subpopulation of cells that produce at least 0.1 mg per g biomass dry weight of the sphingoid base of Formula I.

In the method according to the invention, a population of microbial cells is incubated in the presence of a suitable concentration of a toxin and a subpopulation of cells is isolated (selected) being resistant against said toxin. The toxin that is applied should be toxic to the starting population of microbial cells, i.e. the toxin should have the effect that the cells are unable to grow or to survive when incubated in the presence of a suitable concentration of the toxin. Upon incubation in the presence of a suitable concentration the toxin, a subpopulation of the cells is isolated that displays resistance to the toxin, i.e. is able to grow in the presence of the toxin. A subset of these toxin-resistant cells may have obtained one or more mutations providing, for instance, an improved production level of a sphingoid base according to formula I.

Typical toxins one could apply for such a selection are: syringomycinE, which becomes toxic upon the action of sphinganine hydroxylase (Grilley et al. (1998), J, Biol. Chem. 273, 11062-11068), therefore resistant cells might be sphinganine hydroxylase negative mutants; non-acetylated sphingoid bases as sphinganine, phytosphingosine and sphingosine, which are toxic as growth inhibitors or as apoptosis inducing compounds (Chung et al. (2001), J. Biol. Chem. 276, 35614-35621; Cheng et al. (2003), Mol. Cell. Biol. 23, 163-177), resistant cells might be non-sensitive sphingoid base overproducing cells; fumonisins, which are inhibitors of (dihydro)ceramide synthase, resistant cells might be cells with a increased flux through the sphingoid base biosynthesis pathway (Merill (2002), J. Biol. Chem. 277, 25843-25846); AAL (*Alternaria alternata*) toxins, which are analogues of sphingoid bases, resistant cells might be cells that produce an altered level and/or an altered composition of sphingoid bases (Abbas et al. (1994), Plant Physiol. 106, 1086-1093).

A suitable concentration of the toxin typically lies around the minimal inhibitory concentration (MIC value) found for the microbial cells that are subjected to the method of the invention. The MIC value will be dependent on the microbial cells that are used and may be between for instance 2 and 10 µg/ml. From the toxin-resistant subpopulation of cells, microbial strains are isolated that produce at least 0.1 mg per g biomass dry weight of the sphingoid base according to Formula I.

Surprisingly, it has been found that a high percentage of toxin-resistant cells produces at least 0.1 mg per g biomass dry weight of a sphingoid base according to Formula I.

In particular, it was surprisingly found that use of the toxin syringomycinE resulted in syringomycinE-resistant *Pichia ciferrii* cells that produce high levels of sphinganine. This is surprising, because it is considered unlikely that methods described for a haploid species like *S. cerevisiae* (Grilley et al., supra) would also work for a diploid species like *Pichia ciferrii*, (Wickerham and Burton, 1962, Bacteriol Rev. 26:382-397), especially if such a diploid species further has a high flux towards sphingoid bases.

There are several examples that diploid species are cumbersome for isolating specific mutants on the basis of resistance against toxins. For instance, Nosek et al., (2002, Curr Genet, 42:27-35) describe that no 5-fluoroorotic acid (5-FOA)-resistant clones of the diploid yeast strain *Candida parapsilosis* SR23 could be isolated, even though the cells were subjected to mutagenic treatment prior to incubation in the presence of the toxin. In another publication (Wellington and Rustchenko, 2005, Yeast, 22:57-70) the isolation of 5-FOA-resistant clones of the diploid yeast strain *Candida albicans* is reported. However, these clones remain prototrophic for uracil. Thus, targeted inactivation of the URA3 gene, encoding orotidine-5'-phosphate decarboxylase, by subjection to 5-FOA, which is easily possible in haploid yeast species such as laboratory strains of *Saccharomyces cerevisiae*, appeared to be not possible in diploid yeast strains.

Sphingoid bases, like sphinganine, are known for inducing apoptosis (Cheng et al., 2003, Mol Cell Biol, 23: 163-177). *P. ciferrii* apparently has circumvented this problem via an efficient acetylation and subsequent secretion of phytosphingosine. However, it is unpredictable how such an organism will react when cells would be driven to accumulate sphinganine instead of phytosphingosine.

The population of microbial cells that is subjected to the method of the invention may be a population of identical cells derived from one particular parent strain. In this way, typically spontaneous mutants may be isolated. The population of microbial cells that is subjected to the method of the invention may also be a population of cells that is firstly subjected to a mutagenic treatment to deliberately introduce genetic variation into said population. The mutagenic treatment typically may comprise a so-called classical treatment, but also may include DNA-mediated transformation.

A classical treatment includes protoplast fusion and/or a treatment with UV radiation or certain chemicals.

In one embodiment, microbial cells producing the sphingoid base according to Formula I are isolated from a population of cells that is subjected to a mutagenic treatment but that is not subjected to a toxin treatment prior to mutagenic treatment. This embodiment is particularly useful when the mutagenic treatment is DNA-mediated transformation, more in particular with the aim to engineer the sphingolipid metabolic pathway.

In another embodiment, the mutagenic treatment is done on toxin-resistant cells, preferably on toxin-resistant cells that produce at least 0.1 mg per g biomass dry weight of the sphingoid base according to Formula I. This embodiment is also particularly useful when the mutagenic treatment is DNA-mediated transformation with the aim to engineer the sphingolipid metabolic pathway.

Engineering the sphingolipid metabolic pathway can be done in various ways. For instance by modifying, i.e. increasing or decreasing, the expression level of one or more enzymes from the metabolic pathway. Decreasing the expression level may thereby be effectuated, for instance, by targeted inactivation of the gene encoding the enzyme of interest. Additionally or alternatively, by modifying one or more individual enzymes of the metabolic pathway, for instance to obtain an enzyme with an altered substrate specificity or a higher affinity for a particular substrate.

One example of engineering the sphingolipid metabolic pathway is increasing the expression level of dihydroceramide desaturase, i.e. overexpressing the gene encoding dihydroceramide desaturase, in particular as is provided in a further aspect of this invention.

Another example of engineering the sphingolipid metabolic pathway is the modification of the substrate range of a desaturase enzyme in such away that a sphingoid base, e.g. sphinganine, is the preferred substrate of this enzyme instead of a ceramide (in particular a dihydroceramide), providing for a direct in situ conversion of sphinganine into sphingosine.

Other examples of engineering the sphingolipid metabolic pathway are an alteration of the acetylation pattern of the sphingoid base, an alteration of the chain length composition of the sphingoid base and/or an increased or decreased secretion of the sphingoid base.

Sphingoid bases with an altered acetylation pattern may be obtained by, for instance, screening for and possibly enrichment of mutant strains with a modified acetylation activity and/or a modified secretion activity in such a way that strains are isolated that produce more or less acetylated forms of the sphingoid base according to Formula I as compared to a parent strain.

The present invention further envisages the modification of the activity of dihydroceramide desaturase, optionally in combination with the modification of ceramidase activity, optionally in combination with the modification of an acetylation enzyme, optionally in combination with the modification of an enzyme of the secretion machinery, in such a way that an increased flux from intracellular sphinganine via ceramide towards secreted sphingosine is obtained.

In one embodiment of the invention, microbial strains are isolated that display, as compared to a parent strain, an improved productivity of the sphingoid base according to Formula I and/or a change in expression level and/or intracellular localisation of an enzyme of the sphingolipid metabolic pathway.

An improved productivity of the sphingoid base thereby includes an increase in productivity as compared to the parent strain and/or the production of a sphingoid base that is not substantially produced by the parent strain. A change in expression level of an enzyme of the sphingolipid metabolic pathway thereby includes an increase in expression level as compared to the parent strain and/or expression of an enzyme activity not being expressed in the parent strain.

In the context of the present invention, a parent strain is a strain that does not substantially produce the sphingoid base according to Formula I. For instance, a suitable parent strain may be a strain that produces the sphingoid base according to Formula I at a level that is lower than 0.1 mg per g biomass dry weight, under the specified conditions. A parent strain may also be a strain that produces a substantial amount of a sphingoid base that is excluded from the sphingoid base according to Formula I, such as, preferably, *Pichia ciferrii* NRRL Y-1031 F-60-10 and/or any of the *Pichia ciferrii* strains disclosed in WO 95/12683, all producing predominantly C18-phytosphingosine.

In a third aspect, the present invention provides a polypeptide having dihydroceramide desaturase activity, preferably obtainable from the yeast *Pichia ciferrii*. In particular, the polypeptide of the present invention having dihydroceramide desaturase activity has an amino acid sequence according to SEQ ID NO: 1 and/or has an amino acid sequence having a percentage identity of at least 67% to SEQ ID NO:1, preferably at least 70%, more preferably at least 80%, most preferably at least 90% to SEQ ID NO: 1 (homologous polypeptides). Homologous polypeptides may be naturally occurring variants obtainable from other microbial, in particular yeast, strains, or may be engineered variants.

It was surprisingly found that *Pichia ciferrii*, producing large amounts of phytosphingosine, but no sphingosine, contains a polypeptide displaying sequence similarity to a dihydroceramide desaturase from *Candida albicans*.

The skilled person will be aware of the fact that several different computer programs are available to determine the percentage identity between two sequences. For instance, the percent identity between two amino acid sequences is determined using the Needleman and Wunsch (J. Mol. Biol. (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms. Conveniently, the Blossom 62 matrix is used with the default settings (gap weight is 12, length weight is 1).

The present invention surprisingly shows that microbial cells that display an increased expression level of the polypeptide of the invention as compared to a parent strain display an increased productivity of the sphingoid base according to Formula I. In particular of a sphingoid base according to Formula I, wherein and A-B is CH=CH and R is $(CH_2)_m$—X—$(CH_2)_n$—$CH_3$, wherein, more preferably, m is 0, X is $CH_2$—$CH_2$ or CHOH—$CH_2$, and n is between 8 and 12, most preferably n is 10.

In a fourth aspect, the present invention provides a polynucleotide comprising a nucleotide sequence encoding the polypeptide of the third aspect. Preferably, the polynucleotide comprises a nucleotide sequence encoding the amino acid sequence of SEQ ID NO: 1. More preferably, the nucleotide sequence encoding the amino acid sequence of SEQ ID NO: 1 is SEQ ID NO:2 or contained in SEQ ID NO:3.

In particular, the invention relates to a homologous polynucleotide comprising a nucleotide sequence encoding the polypeptide of the third aspect that is hybridisable under stringent conditions, preferably under highly stringent conditions, to a nucleotide sequence according to SEQ ID NO: 2, or a subsequence thereof.

Advantageously, such homologous polynucleotides may be obtained from a sphingoid base-producing microbial strain, in particular from a sphingoid base-producing yeast strain, more in particular from a *Pichia* strain.

For example, using the nucleic acid sequence of SEQ ID NO: 2 or a subsequence thereof as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, more preferably at least 95% identical to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

In a typical approach, cDNA libraries constructed from an organism of choice can be screened for polynucleotides that are homologous to SEQ ID NO: 2 using a probe derived from SEQ ID NO:2. Upon detection of transcripts homologous to SEQ ID NO: 2, cDNA libraries can be constructed from RNA isolated from the appropriate strain, utilizing standard techniques well known to those of skill in the art. Alternatively, a total genomic DNA library can be screened.

Homologous gene sequences can also be isolated, for example, by performing PCR using two (degenerate) oligonucleotide primer pools designed on the basis of nucleotide sequences as taught herein. The template for the reaction can be chromosomal DNA or cDNA obtained by reverse transcription of mRNA prepared from strains known or suspected to express a polynucleotide according to the invention. The PCR product can be subcloned and sequenced to ensure that the amplified sequences represent the sequences according to the invention. Moreover, a nucleic acid molecule encompassing all or a portion of SEQ ID NO: 2 can be isolated by PCR using synthetic oligonucleotide primers designed based upon the sequence information contained in SEQ ID NO: 2.

The obtained PCR fragment can then be used to isolate a full length cDNA clone by a variety of known methods. For example, the PCR fragment can be labeled and used to screen a cDNA library or a genomic library. Alternatively, an inverse PCR reaction can be applied using DNA sequences of the obtained PCR fragment.

Homologous gene sequences can also be obtained by mutagenesis techniques, preferably applied to SEQ ID NO: 2.

Suitable mutagenesis techniques include random mutagenesis (e.g. error-prone PCR), site-specific mutagenesis and/or gene shuffling. For instance, mutagenesis can be used to obtain a desaturase polypeptide with a higher affinity for its substrate than the competing hydroxylase enzyme, and/or with a higher specific enzyme activity and/or with an altered substrate specificity, for instance with respect to the length of the alkyl chain of the sphingoid base.

The invention also provides vectors comprising a polynucleotide of the fourth aspect, including cloning vectors and expression cassettes.

The vector into which the polynucleotide of the invention is inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid, cosmid, virus or phage vector, usually provided with an origin of replication. Alternatively, the vector may be one which, when introduced into a host cell, is integrated into the host cell genome and replicated together with the chromosome(s) into which it has been integrated. The vector may be a circular, e.g. a plasmid, or a linear, e.g. an expression cassette.

Preferably, the polynucleotide of the invention may be inserted into an expression cassette. In an expression cassette, the polynucleotide of the invention is operably linked to a regulatory sequence that is capable of providing for the expression of a polypeptide from its coding sequence by the host cell. The term "operably linked" refers to a juxtaposition wherein the components described are in a relationship permitting them to function in their intended manner. A regulatory sequence such as a promoter, an enhancer or another expression regulatory signal "operably linked" to a coding sequence is positioned in such a way that expression of a polypeptide from its coding sequence is achieved under conditions compatible with the regulatory sequences.

An expression cassette for a given host cell may comprise the following elements operably linked to each other in appropriate order from the 5'-end to 3'-end relative to the coding strand of the sequence encoding the polypeptide of the first aspect: a promoter sequence capable of directing transcription of the DNA sequence encoding the polypeptide in the given host cell; optionally, a signal sequence capable of directing secretion of the polypeptide from the given host cell into a culture medium; optionally, a targeting sequence for directing the polypeptide to a certain subcellular compartment, a DNA sequence encoding a mature and preferably active form of the polypeptide; and preferably also a transcription termination region (terminator) capable of terminating transcription downstream of the DNA sequence encoding the polypeptide.

Aside from the promoter native to the gene encoding (a naturally occurring predecessor of) the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulatory signals may be selected to be compatible with the host cell for which the expression cassette or vector is designed. Preferably the promoter sequence is derived from an inducible or a highly expressed gene. In the context of this invention, a highly expressed gene is a gene whose mRNA can make up at least 0.01% (w/w) of the total cellular mRNA, e.g. under induced conditions, or alternatively, a gene whose gene product can make up at least 0.2% (w/w) of the total cellular protein, or, in case of a secreted gene product, can be secreted to a level of at least 0.05 g/l. Examples of preferred highly expressed genes from which promoters are preferably derived and/or which are comprised in preferred predetermined target loci for integration of expression cassettes, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, or the plasma membrane H(+)-ATP-ase gene (PMA1) from *Hansenula polymorpha*. Additional yeast promoters include the strong yeast promoters obtainable from the genes for lactase or pyruvate dehydrogenase subunit 1, or promoters from genes from the sphingolipid biosynthetic pathway, e.g. SYR2 (spinganine hydroxylase), LCB1 (serine palmitoyltransferase subunit1), LCB2 (serine palmitoyl-transferase subunit2), TSC10 (keto-dihydrosphingosine reductase), LAC1 (ceramide synthase/sphinganine N acyl-transferase, CoA dependent), LAG1 (ceramide synthase/sphinganine N acyltransferase, CoA dependent), DES1 (desaturase), YDH1 (dihydroceramidase), YPC1 (phytoceramidase), LCB4 (sphingoid lipid kinase), LCB5 (sphingoid lipid kinase).

Downstream of the polynucleotide sequence encoding the polypeptide there may be a 3' untranslated region containing one or more transcription termination sites (e.g. a terminator). The origin of the terminator is less critical. The terminator can e.g. be native to the polynucleotide sequence encoding the polypeptide. However, preferably a yeast terminator is used in yeast host cells and a filamentous fungal terminator is used in filamentous fungal host cells. More preferably, the terminator is endogenous to the host cell (in which the polynucleotide sequence encoding the polypeptide is to be expressed).

The vector may contain one or more selectable marker genes, to enable selection of transformed cells from the majority of untransformed cells.

Preferred selectable markers include but are not limited to those that complement a defect in the host cell or confer resistance to a drug. They include e.g. versatile marker genes that can be used for transformation of most fungi including yeasts such as the acetamidase (amdS) genes or cDNAs, or genes providing resistance to antibiotics, like G418, hygromycinB, bleomycin, nourseothricin, phleomycin, zeocin, blasticidinS, aureobasidinA, bialaphos or cyclohexamide. Alternatively, specific selection markers can be used such as auxotrophic markers that require corresponding mutant host strains: e.g. URA3 (from *S. cerevisiae* or analogous genes from other yeasts), LEU2, HIS3 or TRP1. In a preferred embodiment the selection marker is removed from the transformed host cell after introduction of the expression construct so as to obtain transformed host cells capable of producing the polypeptide which are free of selection marker genes.

The nucleotide sequence encoding the polypeptide is preferably introduced into a suitable host as part of an expression vector or cassette. For transformation of the suitable host with the expression vector or cassette, transformation procedures are available which are well known to the skilled person. The expression cassette can be used for transformation of the host as part of a vector carrying a selectable marker, or the expression cassette may be co-transformed as a separate molecule together with the vector carrying a selectable marker. The vector may comprise one or more selectable marker genes.

For most filamentous fungi and yeasts, the vector or expression construct is preferably integrated in the genome of the host cell in order to obtain stable transformants. However, for certain yeasts also suitable episomal vectors are available into which the expression construct can be incorporated for stable and high level expression. Examples thereof include vectors derived from the 2μ and pKD1 plasmids of *Saccharomyces* and *Kluyveromyces*, respectively. In case the expression constructs are integrated in the genome of the host cell, the constructs are either integrated at random loci in the genome, or at predetermined target loci using homologous recombination, in which case the target loci preferably comprise a highly expressed gene. A number of examples of suitable highly expressed genes are provided earlier. Preferred integration target sites are the rRNA locus (Bae et al, 2003) or the promoter regions of PDA1, ENO1, GAPDH, SYR2.

In a further aspect are provided host cells comprising the polynucleotide of the invention. The polynucleotide may be heterologous to the genome of the host cell. In this context, the term "heterologous" means that the polynucleotide does not naturally occur in the genome of the host cell in the recombinant form wherein it is introduced in the host, or that the host cell does not naturally produce the polypeptide.

Suitable host cells are prokaryotic microorganisms such as bacteria, or eukaryotic organisms, for example fungi, such as yeasts or filamentous fungi. Preferred hosts are are yeasts.

A preferred yeast host cell for the expression of the DNA sequence encoding the polypeptide of the invention is of the genus *Saccharomyces, Kluyveromyces, Hansenula, Pichia, Yarrowia, Candida, Eremothecium*. More preferably a yeast host cell is selected from the group consisting of the species *Saccharomyces cerevisiae, Kluyveromyces lactis, Hansenula polymorpha, Pichia pastoris, Pichia ciferrii, Yarrowia lipolytica, Candida albicans, Candida utilis, Eremothecium gossypii*. Most preferred is the yeast *Pichia ciferrii*.

In an especially preferred embodiment of the invention, the host cell is a toxin-resistant cell as described earlier in this invention.

A further aspect of the invention thus provides host cells transformed with or comprising a polynucleotide or vector of the invention. Preferably the polynucleotide is carried in a vector for replication of the polynucleotide and/or expression of the polypeptide of the invention. The vector will be chosen to be compatible with the host cells of choice. In the embodiment of the invention wherein the host cell is a toxin-resistant cell as described earlier in this invention, the toxin-resistant phenotype may be obtained prior to or after the transformation event.

If the polynucleotides of the invention are incorporated into a recombinant replicable vector, the vector may be used to replicate the polynucleotide in a compatible host cell.

Thus in a further aspect, the invention provides a method of producing a polynucleotide according to the invention by introducing a polynucleotide according to the invention into a replicable vector, introducing the vector into a compatible host cell, and growing the host cell under conditions which bring about replication of the vector. The vector containing the polynucleotide according to the invention may be recovered from the host cell. Suitable host cells include bacteria such as *E. coli*.

In a further aspect the invention provides a process for preparing the polypeptide according to the invention by cultivating a host cell (e.g. transformed with an expression vector as described above) under conditions to provide for expression (by the vector) of the polypeptide according to the invention, and optionally recovering the expressed polypeptide. Preferably the polypeptide is produced as a secreted protein in which case the polynucleotide sequence encoding a mature form of the polypeptide in the expression construct is operably linked to a polynucleotide sequence encoding a signal peptide.

In a further aspect the invention provides a process for preparing a sphingoid base of Formula I by cultivating a microbial cell according to the first aspect of the invention and/or a host cell transformed with a polynucleotide according to the fourth aspect of the invention (e.g. cloned in an expression cassette as described above) under conditions to provide for expression of the sphingoid base and, if necessary, of the polypeptide according to the invention, and optionally recovering the sphingoid base.

The cells according to the invention may be cultured using procedures known in the art. For each combination of a promoter and a host cell, culture conditions are available which are conducive to expression of the polypeptide of the invention. After reaching the desired cell density the culture is stopped and the polypeptide or the sphingoid base of the invention is recovered using known procedures.

The fermentation medium may comprise a known culture medium containing a carbon source (e.g. glucose, maltose, molasses), a nitrogen source (e.g. ammonia, ammonium sulphate, ammonium nitrate, ammonium chloride, organic nitrogen sources e.g. yeast extract, malt extract, peptone), and other inorganic nutrient sources (e.g. phosphate, magnesium, potassium, zinc, iron, etc.). Optionally, an inducer may be included.

The selection of the appropriate medium may be based on the choice of expression host and/or based on the regulatory requirements of the expression construct and/or based on requirements associated with optimal expression of the sphingoid base according to the invention. Such media are known to those skilled in the art.

The fermentation can be performed over a period of 0.5-30 days. It may be a batch, continuous or fed-batch process, suitably at a temperature in the range of between 0 and 45° C. and, for example, at a pH between 2 and 10. Preferred fermentation conditions are a temperature in the range of between 20 and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. The polypeptide and/or sphingoid base of the invention may then be recovered and, if desired, purified and isolated by conventional means.

The present invention advantageously shows that the production of a sphingoid base according to Formula I can be done fully fermentative. In particular, it is shown that sphingosine can be produced fermentatively. Alternatively, sphingosine may be produced chemically from sphinganine that is fermentatively produced according to the invention, or with a biotransformation using a suitable organism modified to express an active sphinganine desaturase polypeptide as described above and fed with sphinganine that is fermentatively produced according to the invention, or by applying a bioconversion using a stably isolated and optionally formulated active sphinganine desaturase enzyme and fed with sphinganine that is fermentatively produced according to the invention, or any combination of the above.

Conveniently, the sphingoid base of the invention may be combined with suitable excipients to produce a sphingoid base composition.

The sphingoid base of the invention may be used as starting material to prepare other sphingoid bases, or sphingolipids, like ceramides, gangliosides or cerebrosides.

EXAMPLE 1

Isolation of Genomic DNA From *Pichia Ciferrii* F-60-10A NRRL 1031

*Pichia ciferrii* F-60-10A NRRL 1031 was grown in 50 ml YEPD medium (peptone 2% (w/v), yeast extract 1% (w/v) and glucose 2% (w/v) in 250 ml Erlenmeyer flasks at 200 rpm and 30° C. and harvested after 18 h at an $OD_{600}$ of 1.5. Chromosomal DNA was isolated using the PUREGENE® DNA Purification Kit for Yeast and Gram-positive bacteria (Gentra Systems Inc., cat.# D-6000A) according to the instructions of the manufacturer. A quality check of the isolated DNA by agarose gel electrophoresis demonstrated its high molecular weight (>16 kbp).

EXAMPLE 2

Amplification of an Internal Part of the *Pichia ciferrii* DES1 Gene

First, the amino acid sequences of putative dihydroceramide $\Delta^4$ desaturases from ascomycetes species were extracted from NCBI's database of completed and unfinshed eukaryotic genomes (www.ncbi.nim.nih.gov/sutils/genom_table.cgi) by performing a TBLASTN search with the *Candida albicans* Des1p protein (GenBank acc.# EAL03178) as template. This protein has been characterized biochemically and been proven to represent a ceramide $\Delta^4$ desaturase (Ternes et al., The Journal of Biological Chemistry, 277:25512-25518, 2002). The extracted sequences (all entries with E-values<$2\times10^{-52}$) were aligned using the ClustalW program (www.ebi.ac.uk/clustalw). Suitable oligonucleotides for amplification of an internal part of the *Pichia ciferrii* DES1 gene were derived by back-translating highly conserved stretches of amino acids within the Des1p sequence taking into account the highly biased *Pichia ciferrii* codon usage. The following oligonucleotides were then synthesized by MWG Biotech (Ebersberg, Germany):

```
des1-deg-fw-2LeuT:
ACW TTY CAA ATH TTN TTY TAY GC    (SEQ ID NO: 4)

des1-deg-rv:
GGR AAA TCA TGA TGY TCR TTA TG    (SEQ ID NO: 5)
```

These oligonucleotides were used to set up a PCR reaction according to Innis et al., (PCR protocols. A guide to methods and applications, 1990, Academic Press) with Herculase® Hotstart DNA polymerase (Stratagene, cat.#600312) according to the instructions of the manufacturer. A 350 bp fragment could be obtained by applying this method. The fragment was purified using the QIAquick PCR Purification Kit (Qiagen, cat.#28106) according to the instructions of the manufacturer.

EXAMPLE 3

Figure 1A:
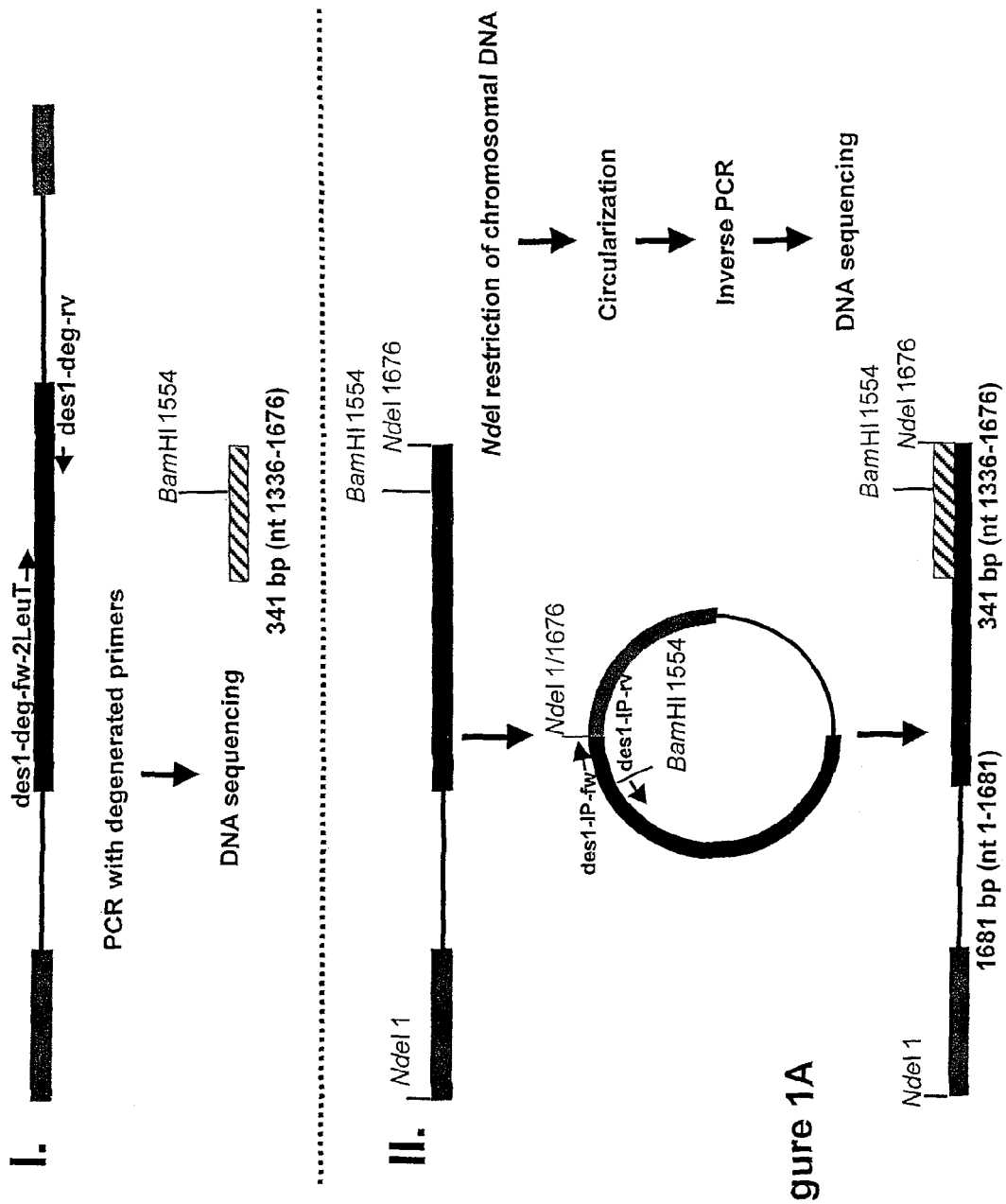
FIGS. 1A and 1B schematically describe the three-step procedure resulting in the isolation of the entire *Pichia ciferrii* DES1 locus. Amplification of an internal part of PcDES1 (I.) was followed by two rounds of inverse PCR (II. and III.) Oligonucleotides used in the individual steps are indicated and sequence representations in different shadings show the portions of the PcDES1 locus whose DNA sequence were determined in the individual steps. Restriction sites relevant for the experimental procedures are also indicated.

Determination of the DNA Sequence of an Internal Part of the *Pichia ciferrii* DES1 Gene The DNA sequence of the purified PCR product was determined using the dideoxy chain termination method developed by Sanger et al. (Proceedings of the National Academy of Sciences, U.S.A., 74:5463-5467). As sequencing primers those used for PCR amplification in Example 1 were used. DNA sequencing was performed by Sequiserve (Vaterstetten, Germany). The generated sequence information (341 bp, corresponding to nt 1336-1676 in SEQ ID NO: 3; FIG. 1A) was translated into protein using the Clone Manager 7 software (Scientific & Educational Software) and the resulting amino acid sequence used as template for a BLASTP search with NCBI's non-redundant protein database (www.ncbi.nlm.nih.gov/BLAST/). The search resulted in the identification of *Candida albicans* Des1p (NCBI acc.# EAL03178) as being the protein in the database most similar to the new sequence, confirming that in fact portions of the *Pichia ciferrii* DES1 ortholog had been amplified.

EXAMPLE 4

Amplification of the Entire *Pichia ciferrii* DES1 Gene and Determination of its DNA Sequence In order to determine the DNA sequence of the entire *Pichia ciferrii* DES1 gene (coding sequence, promoter region and 3'-untranslated region) an inverse PCR approach was followed. Chromosomal DNA (300 ng) from *Pichia ciferrii* F-60-10A NRRL 1031 (isolated as described in Example 1) was digested overnight with NdeI (MBI Fermentas, cat.# ER0581) according to the instructions of the manufacturer in a total volume of 100 µl. The digested DNA was purified using the QIAquick PCR Purification Kit (Qiagen, cat.#28106) according to the instructions of the manufacturer. The eluted DNA (50 µl) was subjected to overnight ligation using the Rapid DNA Ligation Kit (Roche Diagnostics, cat.#1635379) according to the instructions of the manufacturer in a total volume of 200 µl with 1 U of T4 DNA ligase. The ligated DNA was purified using the MinElute Gel Extraction Kit (Qiagen, cat.#28604) according to the instructions of the manufacturer. 1 µl of the eluate was used as template for a inverse PCR reaction according to Innis et al., (PCR protocols. A guide to methods and applications, 1990, Academic Press). For this two oligonucleotides targeted on the already known portion of the *Pichia ciferrii* DES1 gene (see example 3) were applied:

```
des1-IP-fw:
                                 (SEQ ID NO: 6)
AAA GAT CAT CCA CCT TTA GAA ACT TAT TC des1-IP-rv:
                                 (SEQ ID NO: 7)
GAC CTG AAC ATG GAT GTA AAG AAC CAG
```

Amplification was performed with Herculase® Hotstart DNA polymerase according to the instructions of the manufacturer. Using this procedure a 1.6 kbp PCR product could be obtained. The fragment was purified using the QIAquick PCR Purification Kit according to the instructions of the manufacturer. The DNA sequence of this fragment was determined as described in Example 3, using oligonucleotides des1-IP-fw, des1-IP-rv and

Figure 1B:
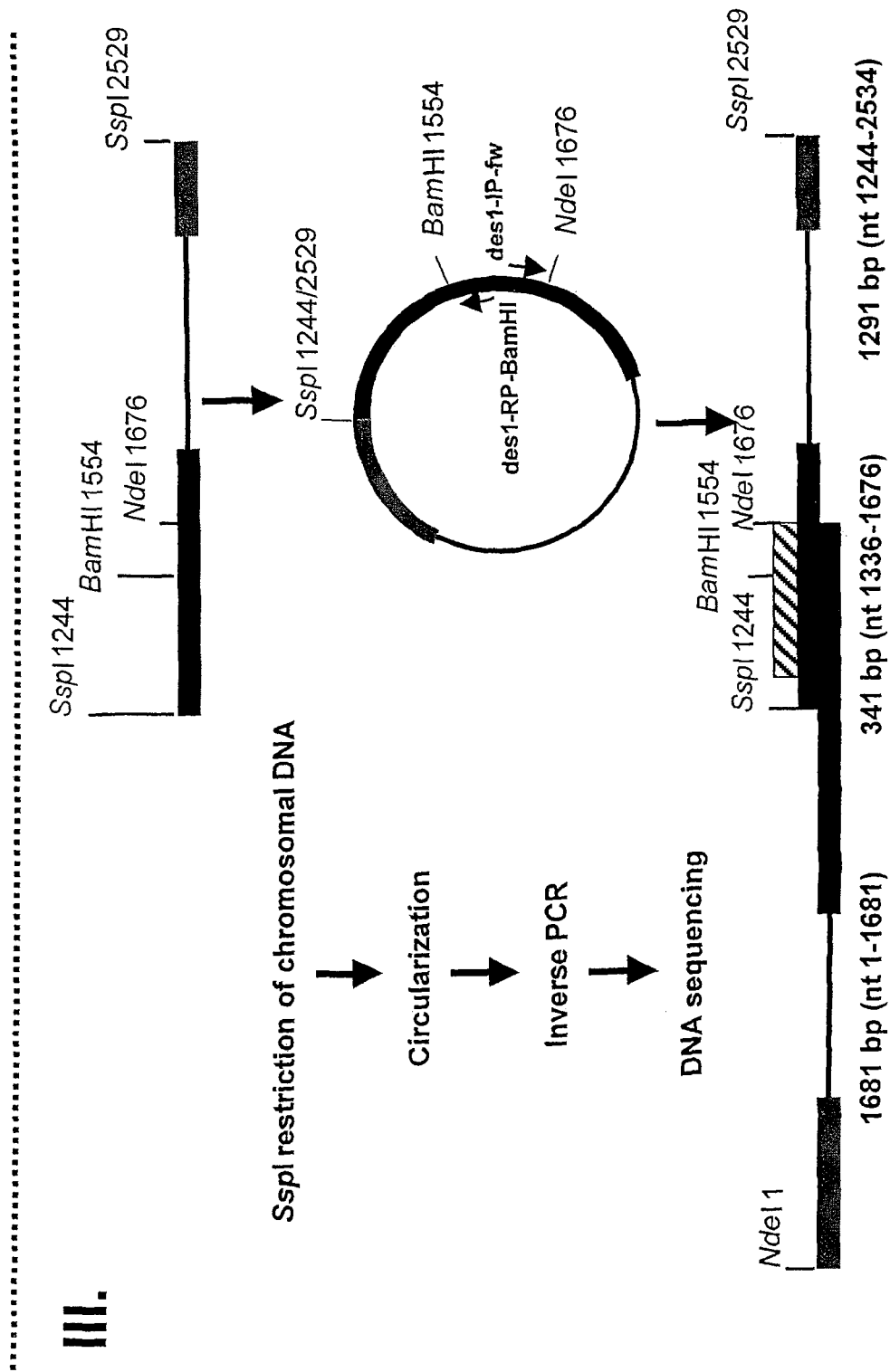

```
SSc-IPfw1:
TTT TTA CTT TTG CGA ATC G        (SEQ ID NO: 8)
``` as sequencing primers. The newly obtained sequence information covered nt 1-1681 in SEQ ID NO: 3 and is flanked by two NdeI sites as had to be expected because of the NdeI digestion of the template DNA. No new sequence information downstream of the DNA sequence obtained in Example 3 could be obtained as the 3' NdeI site is located immediately downstream of this portion (FIG. 1B). In order to obtain the DNA sequence of the 3'-end of the coding region of the *Pichia ciferrii* DES1 gene and its 3'-untranslated region another round of inverse PCR had to be performed. Therefore, the above described experimental protocol was repeated, except that SspI (New England Biolabs, cat.# R0132S) was used for digesting *Pichia ciferrii* chromosomal DNA and the following oligonucleotides, synthesized by MWG Biotech (Ebersberg, Germany), were employed during inverse PCR:

```
des1-IP-fw:
                                 (SEQ ID NO: 9)
AAA GAT CAT CCA CCT TTA GAA ACT TAT TC
```

-continued des1-RP-BamHI:

(SEQ ID NO: 10)
CTG TTA TAA GTC TTT GGT GGA TCC

Using this procedure a 1.2 kbp PCR product could be obtained. The fragment was purified using the QIAquick PCR Purification Kit according to the instructions of the manufacturer. The DNA sequence of this fragment was determined as described in Example 3 with the oligonucleotides des1-IP-fw and des1-RP-BamHI as sequencing primers. 852 bp of new sequence information (nt 1682-2534 in SEQ ID NO: 3) could be obtained which stretches to the next SspI restriction site downstream of the 3′ NdeI site (FIG. 1B). Using the described three-step procedure, a total of 2534 bp of the *Pichia ciferrii* DES1 locus could be isolated and its DNA sequence be determined (see SEQ ID NO: 3 and FIG. 1).

Figure 2:
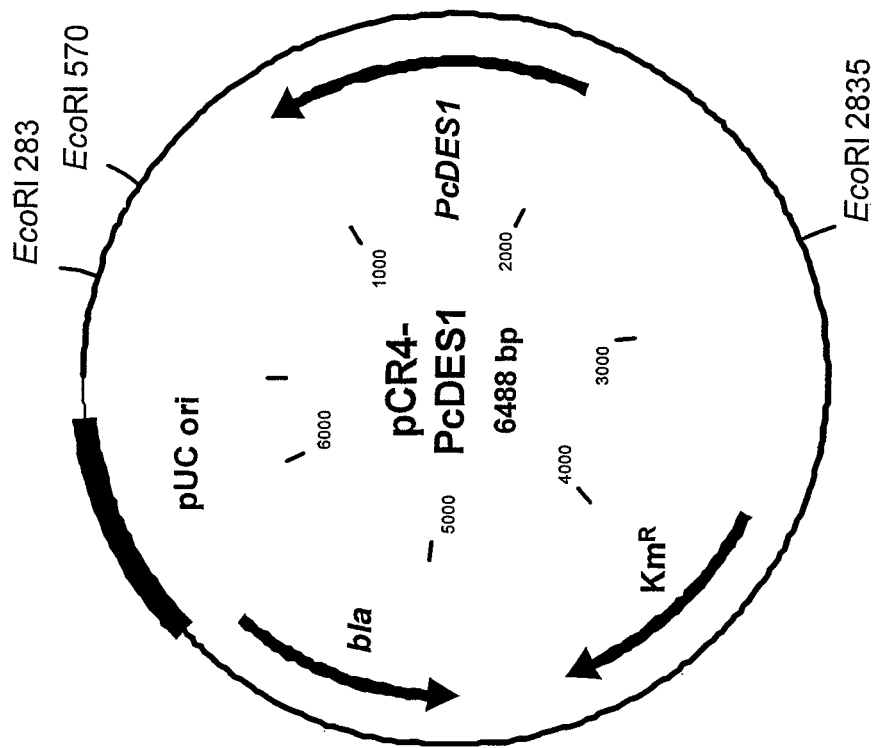
FIG. 2 shows a graphical representation of the *Pichia ciferrii* DES1 locus on the plasmid pCR-PcDES1. The arrows indicate localization and orientation of the open reading frames PcDES1 (hatched arrow, derived from *Pichia ciferrii*), bla (ampicillin resistance gene) and the kanamycin resistance gene (hatched arrows, derived from vector pCR®4-TOPO®). They grey bar indicates the localization of the *E. coli* origin of replication. Restriction sites relevant for cloning and restriction analysis are also shown.

The *Pichia ciferrii* DES1 locus as depicted in FIG. 2 encodes the PcDes1 p protein of 351 amino acids in length (SEQ ID NO: 1). PcDes1p has 62% (76%) and 53% (70%) positional amino acid identity (similarity) to the Des1p proteins from *Candida albicans* (GenBank acc.# EAL03178) and *Schizosaccharomyces pombe* (GenBank acc.#059715), respectively. The Des1p proteins from *Candida albicans* and from *Schizosaccharomyces pombe* have been characterized biochemically and been shown to display dihydroceramide $\Delta^4$ desaturase activity in vivo. PcDes1p contains amino acid sequence motifs typical for lipid desaturases/hydroxylases (Sperling & Heinz, Biochimica and Biophysica Acta, 2003, 1632:1-15): HXXHH (aa 149-153) and HXXHH (aa 291-295). Moreover, PcDes1p is predicted to harbour three transmembrane segments (aa 87-109, 171-193 and 205-227; predicted by the TMHMM tool, www.cbs.dtu.dk/services/TMHMM/), and displays a dilysyl motif at its C-terminal end, possibly serving as endoplasmic reticulum retention signal (Andersson et al., 1999, The Journal of Biological Chemistry, 274:15080-4). The bioinformatic analyses strongly indicate that PCDES1 codes for the *Pichia ciferrii* dihydroceramide $\Delta^4$ desaturase.

EXAMPLE 5

Isolation of SyringomycinE Resistent *Pichia ciferrii* Mutants

In order to isolate high sphinganine producing *Pichia ciferrii* strains the following procedure was followed. First, the natural sensitivity of *Pichia ciferrii* strains for the toxic compound SyringomycinE, produced by *Streptomyces syringae* (Gross D C, 1985, Regulation of syringomycin synthesis in *Pseudomonas syringae* pv. *syringae* and defined conditions for its production. J Appl Bacteriol. 58:167-174), was determined by adding different concentrations of SyringomycinE to agar plates. A stock solution of 3.5 mg SyringomycinE (obtained from J. Takemoto, Utah State University) was prepared by dissolving it in 1.0 ml 0.001 N HCl. The pH was kept below 7 for stability and stored at −20° C. The minimal inhibitory concentration (=MIC-value) for *Pichia ciferrii* strains was determined by using YEPD plates (per liter: Yeast Extract, 10 g; Pepton, 20 g; Glucose, 20 g; Agar, 20 g) containing various concentrations between 0.1 and 20 µg/ml syringomycinE. On each plate with the different concentrations of syringomycinE 100 µl of a freshly grown culture ($OD_{600\,nm}$=0.4) was plated and incubated at 30° C. for 5 days.

Depending on the strain no colonies appeared on plates with 2 to 10 µg/ml of SyringomycinE, meaning that the MIC value lies between 2 and 10 µg/ml.

To isolate SyringomycinE resistant *P. ciferrii* variants selective plates with 10 µg/ml in YEPD were chosen, as this concentration was demonstrated to be lethal to standard *P. ciferrii* strains and strains that would survive on these plates could be nominated as 'resistant strains'. If lower concentrations are used this will result in background growth of the non-resistant colonies, hampering the isolation of real resistant mutants. To isolate SyringomycinE resistant *P. ciferrii* variants phytosphingosine producing strains of *P. ciferrii*, as described in U.S. Pat. No. 6,204,006 (De Boer L and Van der Wildt I F C, Microbial strains producing sphingolipid bases), were pre-grown in a liquid YEPD culture till an $OD_{600\,nm}$=1.0 and different aliquots were plated out on 10 µg/ml SyringomycinE plates and incubated at 30° C. for 5 days. The 25 colonies appearing as spontaneous SyringomycinE resistant isolates on these plates were transferred to standard YEPD plates, which could serve as so-called master plates. After the non-selective growth on these YEPD plates all isolates were re-tested on YEPD plates with either 10 µg/ml or 15 µg/ml SyringomycinE. Ten of the primary isolates that could grow on 10 µg/ml and even on 15 µg/ml SyringomycinE were nominated as true 'resistant' isolates. These ten isolates were colony purified on standard YEPD plates and stored for later applications.

EXAMPLE 6

Shake Flask Production of Sphinganine by SyringomycinE Resistent *Pichia ciferrii* Mutants To assess the sphingoid base production by the *Pichia ciferrii* syringomycinE mutants, isolated as described in example 5, pre-cultures of all ten true resistant isolates were inoculated in 25 ml YEPD (in a 100 ml Erlenmeyer flask, without baffle) at 300° C. and 280 rotations per minute for 3 days. Subsequently, 1% of the preculture was used to inoculate 100 ml LCBNB (in a 500 ml Erlenmeyer flask, with baffle) and grown) at 300° C. and 280 rotations per minute for 4 days.

TABLE 1

| Composition of LCBNB (= Long chain base nutrient broth) medium | | |
|---|---|---|
| Component | Formula | per liter |
| Yeast extract | — | 0.7 g |
| Dextrose | $C_6H_{12}O_6 \cdot 1aq$ | 44 g |
| Magnesium sulfate•7aq | $MgSO_4 \cdot 7H_2O$ | 0.88 g |
| Calcium chloride•2aq | $CaCl_2 \cdot 2H_2O$ | 0.20 g |
| Ammonium chloride | $NH_4Cl$ | 4.83 g |
| Sodium chloride | NaCl | 0.30 g |
| Potassium dihydrogen phosphate | $KH_2PO_4$ | 1.0 g |
| Potassium dihydrogen phthalate | $KH_2C_8H_4O_4$ | 20 g |
| Antifoam (synperonic) | — | 0.40 ml |
| Trace elements | Sol. B | 0.30 ml |
| Vitamin solution | Sol. B | 1.50 ml |

TABLE 2

| Composition of Trace and vitamins stock solutions | |
|---|---|
| Trace elements | Solution B (g/kg) |
| 96% $H_2SO_4$ | 20 ml |
| ascorbic acic•$1H_2O$ | 50 g |
| $FeSO_4 \cdot 7H_2O$ | 48 g |
| $ZnSO_4 \cdot 7H_2O$ | 16.7 g |
| $CuSO_4 \cdot 7H_2O$ | 2.5 g |

TABLE 2-continued

Composition of Trace and vitamins stock solutions

| | |
|---|---|
| $MnSO_4 \cdot 1H_2O$ | 1.88 g |
| $H_3BO_3$ | 2 g |
| $NaMoO_4 \cdot 2H_2O$ | 2 g |
| KI | 0.5 g |

| Vitamine solution | Solution B |
|---|---|
| 96% $H_2SO_4$ | 3.6 ml |
| Nicotinic acid | 2 g |
| Calcium-D-pantothenaat | 2 g |
| Thiamin (vitamin B1) | 2 g |
| Pyridoxin (vitamin B6) | 0.32 g |
| d-Biotin Solution of 1 g/kg | 0.016 g |

For the determination of acetylated sphingoid bases (e.g. long chain bases like phytosphingosine, sphingosine and sphinganine) 2.5 gram of total fermentation broth was transferred to a 25 ml volumetric flask. Then 2.5 ml of purified water and 12 ml acetone were added. The flask was mixed for 10 minutes to extract the lipids and afterwards filled up with acetone to 25 ml. Two ml of the solution was centrifuged at 10.000 rpm for 10 minutes. 10 µl was injected onto the column. The samples were analysed using a 2695 HPLC system Waters and a column from GL Science (Inertsil ODS-80A, 4.6×250 mm). The mobile phase consisted of 0.05% TFA in acetonitrile. The flow was 1 ml/min with UV detection at 200 nm. The conditions used were:

| | |
|---|---|
| Flow | 1.0 ml/min |
| Injection volume | 10 µl |
| Column temperature | Ambient |
| Tray temperature | Ambient |
| UV | 200 nm |
| Mobile phase | 0.05% TFA in acetonitrile |
| Dilution buffer | Water/Acetone (10:90) |

Figure 3:
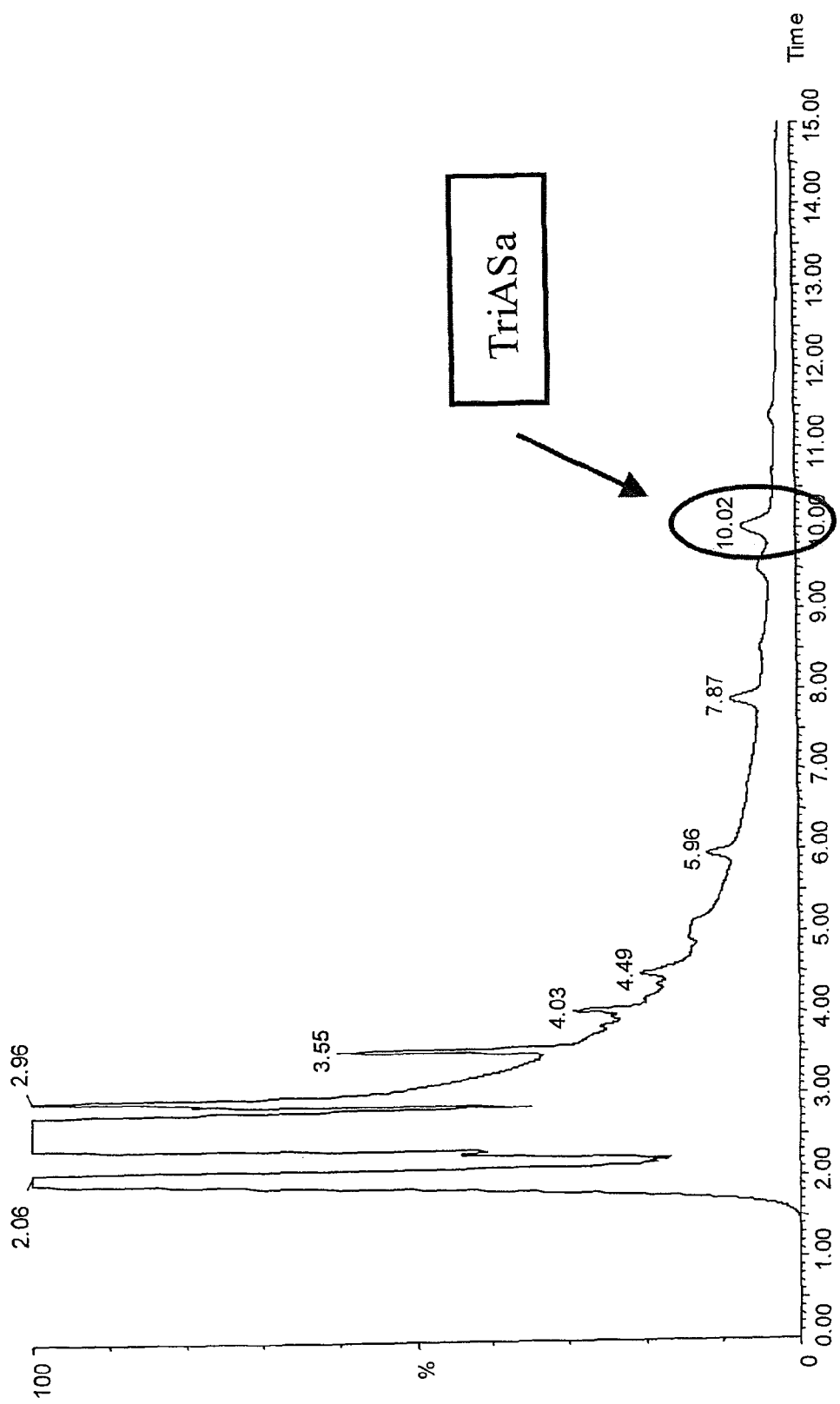
FIG. 3 shows a typical chromatography plot after LC-UV analysis of fermentation broth confirming the presence of triacetylated sphinganine, TriASa.

As controls commercially available LCBs were acetylated and used. Triacetylated sphinganine, indicated as TriASa, could be detected in the fermentation broth (FIG. 3). Typical concentrations of (acetylated) sphinganine that were found to be produced by the selected syringomycinE resistant mutants range from 10-100 mg per g biomass dry weight.

EXAMPLE 7

Identification of Sphinganine By LC-MS

To confirm the presence of acetylated sphinganine, LC-MS was used. Standard sphinganine and phytosphingosine (as control) were acetylated with acetylating reagent. The acetylating reagent contained 40 mg 4-dimethylaminopyridin, 0.6 ml acetic acid anhydride and 0.2 ml triethylamine dissolved in 10 ml ethanol free chloroform. As standards about 3-4 mg of the sphingoid bases were dissolved in 10 ml acetonitril. To 0.8 ml sphingoid base solution, 0.2 ml acetylating reagent was added. After 20-25 minutes reaction time at room temperature, 5 µl was injected. The triacetylated form of Sphinganine (TriASa) could be detected.

LC-UV-MS Details

| Instrument: | LC-ZQ from Waters (CV18) |
|---|---|
| MS | ESI/pos |
| Capillary voltage | 3.66 kV |
| Cone voltage | 24 V |
| Extractor voltage | 2 V |
| RF lens voltage | 0.1 V |
| Desolvation temp | 350° C. |
| Source temp | 130° C. |
| Desolvation gas flow | 600 L/Hr |
| Cone gas flow | 120 L/Hr |
| Ion energy | 0.1 |
| Multiplier | 650 V |
| Scanning | MS mode m/z 400-800 |
| UV | 200 nm |
| Column | YMC J'sphere ODS-H80, 4 µm 250 * 4.6 mm |

Conditions

| | |
|---|---|
| Flow | 1.0 ml/min |
| Injection volume | 5 µl full loop |
| Column temperature | 20° C. |
| Tray temperature | Ambient |
| Divert valve | 1 min to waste |
| Mobile phase | 0.05% TFA in acetonitril |
| Dilution buffer | Water/Acetone (10:90) |

TABLE 3

MS identification of triacetylated sphinagine (TriASa)
RT = 10.02 min tri-acetylsphinganine (TriASa) $C_{24}H_{45}NO_5$ = 427,618

| Observed m/z value | Possible ion Identity |
|---|---|
| 466.3 | $[M + K]^+$ |
| 450.4 | $[M + Na]^+$ |
| 428.4 | $[M + H]^+$ |
| 368.4 | $[M + H - CH_3COOH]^+$ |

EXAMPLE 8

Chain Length of Sphinganine Variants Produced by *Pichia ciferrii*

The isolated strains are capable of producing and excreting Sa and/or its acetylated forms as shown in examples 6 and 7. The chain length of LCBs can vary depending on the efficiency of fatty acid synthesis. The chain lengths of sphinganine (Sa) and its acetylated forms obtained from fermentation broth have been determined with LC-MS. Sa and its derivatives mainly exist of the optimal chain lengths of C18.

TABLE 4 retention times for (acetylated) Sa and TAPS.

| Chain Length | Sa (min) | NASa (min) | DiASa (min) | TriASa (min) | TAPS (min) |
|---|---|---|---|---|---|
| 16 | 2.1 | 6.8 | 10.5 | 14.9 | 14.0 |
| 17 | 2.6 | 8.6 | 12.7 | 17.2 | 16.3 |
| 18 | 3.1 | 10.7 | 15.1 | 19.5 | 18.6 |
| 19 | 3.9 | 12.9 | 17.5 | 21.8 | 20.8 |
| 20 | 4.8 | 15.5 | 19.9 | 24.1 | 23.0 |

TABLE 5 ratio of the different chain lenghts of (acetylated) Sa and TAPS

| Chain length | Sa (%) | NASa (%) | DiASa (%) | TriASa (%) | TAPS (%) |
|---|---|---|---|---|---|
| 16 | 0.3 | 0.0 | 0.1 | 1.8 | nd |
| 17 | 0.2 | 0.0 | 0.1 | 1.1 | nd |
| 18 | 90.2 | 100.0 | 96.5 | 93.8 | nd |
| 19 | 1.8 | 0.0 | 1.0 | 1.5 | nd |
| 20 | 7.6 | 0.0 | 2.3 | 1.8 | nd | nd = not detected

EXAMPLE 9

Composition of Sphinganine Variants Produced by *Pichia ciferrii*

The isolated strains are capable of producing and excreting Sa and/or its acetylated forms. The degree of acetylation can vary from 0 to 3 resulting in respectively:
 sphinganine (Sa)
 monoacetyl sphinganine (NASa)
 diacetyl sphinganine (DiASa)
 triacetyl sphinganine (TriASa)

The relative composition of sphinganine (Sa) and its acetylated forms obtained from a typical fermentation broth have been determined with LC-MS. The samples consist for 50% of fully acetylated TriASa. The second major fraction is DiASa and the minor component is free Sa.

TABLE 6 relative contribution of the different (acetylated) components in both samples

| | Sa (%) | NASa (%) | DiASa (%) | TriASa (%) | TAPS (%) |
|---|---|---|---|---|---|
| Sample Sa producing strain | 9 | 0 | 37 | 55 | 0 |

EXAMPLE 10

Isolating Stable Sphinganine Producing *Pichia ciferrii* Mutants

As *Pichia ciferrii* is a diploid species, the mutation causing resistance to syringomycinE could not be stable. In order to isolate stable sphinganine producing *Pichia ciferrii* strains the following procedure was followed. Selected syringomycinE resistant colonies were colony purified on non-selective YEPD agar to induce good growth. Subsequently, 10 isolates of two different primary syringomycinE resistant colonies were tested in shake flask as described in example 6.

Figure 4:
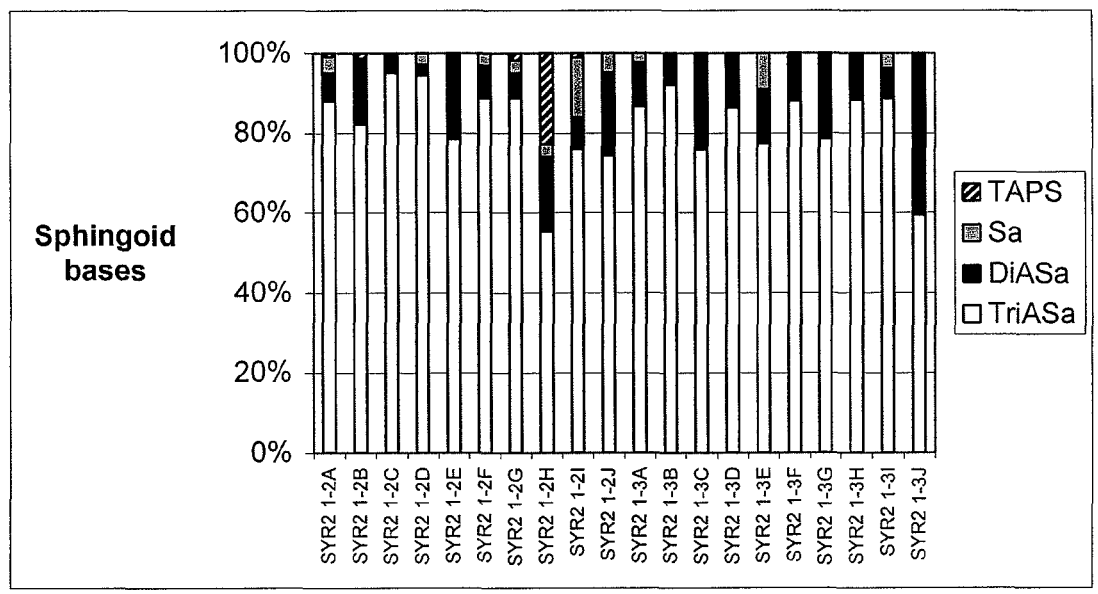
FIG. 4 shows the composition of sphingoid bases produced by ten stable isolates from syringomycinE resistant colonies (TAPS=tetra acetylated phytosphingosine; Sa=sphinganine; DiASa=di-acetylated sphinganine; TriASa=tri-acetylated sphinganine).

The isolates show a different spectrum of sphingoid bases produced, including cell lines that still produce tetra-acetylated phytosphingosine (see FIG. 4; SYR2 1-2H). Using this method it is possible to isolate stable and exclusively sphinganine producing cell lines.

EXAMPLE 11

Construction of a SyringomycinE-Resistant *Pichia ciferrii* Strain Overexpressing the Dihydroceramide Desaturase Gene In order to construct a syringomycinE-resistant mutant overexpressing the *Pichia ciferrii* dihydroceramide desaturase gene we first constructed an integrative DES1 expression vector containing a selection marker, a DNA sequence used for homologous integration of the linearized vector into the chromosomal DNA of *Pichia ciferrii*.

A ribosomal DNA intergenic spacer was chosen as chromosomal integration site. For insertion of the ribosomal DNA intergenic spacer and generation of a unique PmeI recognition sequence within that very integration site, two fragments of the 5S-26S rDNA intergenic spacer (IS) (Bae et al., Integrative transformation system for the metabolic engineering of the sphingoid base-producing yeast *Pichia ciferrii*. 2003. Applied and Environmental Microbiology; U.S. Pat. No. 6,638,735) were amplified by PCR according to Innis et al. (PCR protocols. A guide to methods and applications, 1990, Academic Press) using 200 ng of chromosomal DNA of *Pichia ciferrii* F-60-10A NRRL 1031 as template and the following oligonucleotides:

Fragment 1 pIS-NdeI-rev: 5'-TATATACATATGGCTAGATTGACAGMGTCGATCAG-3' [including a NdeI recognition sequence (underlined) at the 5' end)] (SEQ ID NO: 11)

PmeI-rv: 5'-CCCATCCACTAAGTTTAAACACCCATACAAAATCGAGCTTCAAATC-3' [including a 21 bp sequence at the 5' end complementary to the oligonucleotide PmeI-fw (italicized) and a PmeI recognition sequence (underlined)] (SEQ ID NO: 12)

Fragment 2 p-IS-NdeI-for: 5'-TATATACATATGCTAATCACAACAGAACATTCTCTAACG-3' [including a NdeI recognition sequence (underlined) at the 5' end] (SEQ ID NO: 13)

PmeI-fw: 5'-TGTTTAAACTTAGTGGATGGGAAACCCTGTAG-AACTGGGACAAAC-3' [including a 21 bp sequence at the 5' end complementary to the oligonucleotide PmeI-rv (italicized) and a PmeI recognition sequence (underlined)] (SEQ ID NO: 14)

The obtained PCR fragments (503 and 519 bp, respectively) were purified using the QIAquick PCR Purification Kit according to the instructions of the manufacturer. Subsequently, a fusion of fragments 1 and 2 was obtained by setting up a PCR according to Innis et al. (PCR protocols. A guide to methods and applications, 1990, Academic Press) with 10 ng of each of the two PCR products representing the 5' and 3' portions of the *Pichia ciferrii* 5S-26S rDNA intergenic spacer as templates with oligonucleotides:

p-IS-NdeI-for: 5'-TATATA CATATGCTAATCACAACAGAACATTCTCTAACG-3' [including a NdeI recognition sequence (underlined) at the 5' end] (SEQ ID NO: 15)

pIS-NdeI-rev: 5'-TATATA CATATGGCTAGATTGACAGAAGTCGATCAG-3' [including a NdeI recognition sequence (underlined) at the 5' end] (SEQ ID NO: 16)

The resulting 1 kbp PCR fragment contained NdeI recognition sequences at both ends and a PmeI recognition sequence in the centre of the fragment. The fragment was purified using the QIAquick PCR Purification Kit according to the instructions of the manufacturer. PCR product and vector pAG25 (Goldstein et al., Three new dominant gene disruption cassettes for gene disruption in *Saccharomyces cerevisiae*, 1999, Yeast) were cut with NdeI (according to the instructions of the manufacturer of the restriction endonuclease: New England Biolabs, Schwalbach, Germany). Ligation was performed to generate vector pTH-IS2-PmeI. The orientation and authenticity of the insert was determined by DNA sequencing. Ligation, preparation and transformation of chemically competent *Escherichia coli* cells was performed by methods known to the skilled person.

For construction of a DES1 overexpression cassette the DES1 gene from *Pichia ciferrii* was brought under control of the promoter region of the pyruvate dehydrogenase subunit A gene (PDA1) of *Pichia ciferrii*. First, PcDES1 was amplified using 200 ng of chromosomal DNA of *Pichia ciferrii* F-60-10A NRRL 1031 as template for a PCR according to Innis et al. (PCR protocols. A guide to methods and applications, 1990, Academic Press) with the following oligonucleotides:

DES1-fw: 5'-TAGAAGTTCCAGAAACTACTTTCCAAACTTCAAAATCAACTTTATTATCAATGGCTACAATTACACATAGAAAAAACCCTTCACAAC-3' [including a 50 base sequence at the 5' end complementary to the oligonucleotide PDA1-rv (italicized)] (SEQ ID NO: 17)

DES1-rv: 5'-TATACTGCAGGCATATTGTCMTTCTATTGTACTTGAGTATTAATGATTA-3' [including a PstI recognition sequence (underlined) at the 5' end] (SEQ ID NO: 18)

Accordingly, the promoter region of the pyruvate dehydrogenase subunit A gene of *Pichia ciferrii* (PDA1) was amplified with the following oligonucleotides:

PDA1-fw: 5'-TATACTGCAGTGTGCTCTAAATTTGCCCGGTTCGCGACG-3' [including a PstI recognition sequence (underlined) at the 5' end] (SEQ ID NO: 19)

PDA1-rv: 5'-TGATAATAAAGTTGATTTTGAAGTTTGGAAAGTAGTTTCTGGAACTTCTA-3' (complementary to the 5' end of oligonucleotide DES1-fw) (SEQ ID NO: 20)

The obtained PCR fragments (687 bp and 1596 bp, respectively) were purified using the QIAquick PCR Purification Kit according to the instructions of the manufacturer. Subsequently, a fusion of the PDA1 promoter region and the DES1 gene was obtained by setting up a PCR according to Innis et al. (PCR protocols. A guide to methods and applications, 1990, Academic Press) with 10 ng of each of the two PCR products representing the *Pichia ciferrii* DES1 gene and the *Pichia ciferrii* PDA1 promoter region as template and the following oligonucleotides:

PDA1-fw: 5'-TATACTGCAGTGTGCTCTAAATTTGCCCGGTTCGCGACG-3' [including a PstI recognition sequence (underlined) at the 5' end] (SEQ ID NO: 21)

DES1-rv: 5'-TATACTGCAGGCATATTGTCAATTCTATTGTACTTGAGTATTAATGATTA-3' [including a PstI recognition sequence (underlined) at the 5' end] (SEQ ID NO: 22)

Using this procedure a 2.2 kbp PCR product could be obtained. The fragment was purified using the QIAquick PCR Purification Kit according to the instructions of the manufacturer. Then the PCR product was subjected to digestion with the restriction endonuclease PstI (according to the instructions of the manufacturer of the restriction endonuclease: New England Biolabs, Schwalbach, Germany) and ligated into PstI cut vector pTH-IS2-PmeI (see above) to give pTH-DES1-IS2-PmeI. The orientation and authenticity of the insert was determined by DNA sequencing. Ligation, preparation and transformation of chemically competent *Escherichia coli* cells was performed by methods known to the skilled person.

As selectable marker a cycloheximide resistance conferring resistance cassette based on the *Pichia ciferrii* gene encoding the ribosomal protein L41 was constructed (Bae et al., Integrative transformation system for the metabolic engineering of the sphingoid base-producing yeast *Pichia ciferrii*. 2003. Applied and Environmental Microbiology; U.S. Pat. No. 6,638,735). Two fragments of the *Pichia ciferrii* gene encoding the ribosomal protein L41 were amplified by PCR according to Innis et al. (PCR protocols. A guide to methods and applications, 1990, Academic Press) in order to derive a modified L41* gene using genomic DNA of *Pichia ciferrii* F-60-10A NRRL 1031 as template and the following oligonucleotides:

Fragment 1

PcL41-SalI-fw: 5'-TATAGTCGACGAATTCTCTTAAATGATGTTGG-3' [including a SalI recognition sequence (underlined) at the 5' end] (SEQ ID NO: 23)

PcL41-internal-rv 5'-GTTTTAGCTTTTTTATGGAAAACTTGTTTGGTTTGACCACCGTAACCGG-3' [complementary to the 5' end of oligonucleotide PcL41-internal-fw and inserting a point mutation (C to A; in bold) replacing amino acid residue 56 of the L41 protein from *Pichia ciferrii* (proline to glutamine) resulting in cycloheximide resistance) (Bae et al., Integrative transformation system for the metabolic engineering of the sphingoid base-producing yeast *Pichia ciferrii*. 2003. Applied and Environmental Microbiology; U.S. Pat. No. 6,638,735)] (SEQ ID NO: 24)

Fragment 2

PcL41-internal-fw: 5'-CCGGTTACGGTGGTCAAACCAAACAAGTTTTCCATAAAAAAGCTAAAACTACCAA AAAAGTTGTTTTACG-3' [including a 49 bp sequence at the 5' end complementary to the oligonucleotide PcL41-internal-rv inserting a point mutation (C to A; in bold) replacing amino acid residue 56 of in the L41 protein from *Pichia ciferrii* (proline to glutamine) resulting in cycloheximide resistance) (Bae et al., Integrative transformation system for the metabolic engineering of the sphingoid base-producing yeast *Pichia ciferrii*. 2003. Applied and Environmental Microbiology; U.S. Pat. No. 6,638,735)] (SEQ ID NO: 25)

PcL41-SacI-rv: 5'-TATAGAGCTCAATTCCAATGTTTTGATCTGTC-3' [including a SacI recognition sequence (underlined) at the 5' end] (SEQ ID NO: 26)

The obtained PCR fragments (1222 bp and 753 bp, respectively) were purified using the QIAquick PCR Purification Kit according to the instructions of the manufacturer. Subsequently, a fusion of the two fragments representing a modified L41* gene, mediating cycloheximide resistance was obtained by setting up a PCR with 10 ng of each of the two PCR products with oligonucleotides:

PcL41-SalI-fw: 5'-TATA GTCGACGAATTCTCTTAAATGATGTTGG-3' (including a SalI recognition sequence at the 5' end) (SEQ ID NO: 27)

PcL41-SacI-rv: 5'-TATA GAGCTCAATTCCAATGTTTTGATCTGTC-3' (including a SacI recognition sequence at the 5' end) (SEQ ID NO: 28)

The resulting 1.9 kbp PCR fragment was purified using the QIAquick PCR Purification Kit according to the instructions of the manufacturer. Then the PCR product was subjected to digestion with the restriction endonucleases SalI and SacI (according to the instructions of the manufacturer of the restriction endonucleases: New England Biolabs, Schwalbach, Germany) and ligated into respectively pTH-DES1-IS2-PmeI (see above) to generate vector pDB007 (FIG. 4). The orientation and authenticity of the insert was determined by DNA sequencing. Ligation, preparation and transformation of chemically competent *Escherichia coli* cells was performed by methods known to the skilled person.

Vector pDB007 was linearized with PmeI (according to the instructions of the manufacturer of the restriction endonuclease: New England Biolabs, Schwalbach, Germany) and then purified using the QIAquick PCR Purification Kit according to the instructions of the manufacturer.

Transformation of *Pichia ciferrii* F-60-10A NRRL 1031 cells was performed as described recently (Bae et al., Integrative transformation system for the metabolic engineering of the sphingoid base-producing yeast *Pichia ciferrii*. 2003. Appl Environ Microbiol.; U.S. Pat. No. 6,638,735).

SyringomycinE-resistant *Pichia ciferrii* (described in Example 5) were grown in YEPD medium to an optical density at 600 nm of 1 to 1.5. The cells were harvested by centrifugation and resuspended in 0.1 culture volume of 50 mM phosphate buffer (pH 7.5) to which 25 mM dithiothreitol had been added prior to use. After incubation at 37° C. for 15 min, the cells were washed twice with one culture volume of cold stabilization solution [270 mM sucrose, 10 mM Tris-HCl (pH 7.5), 1 mM $MgCl_2$] and resuspended in 0.01 culture volume of stabilization solution. 5 µl of linearized vector pDB007 (containing 1.6 µg DNA) were mixed with 50 µl of cells and incubated on ice for 10 min. Then the transformation mixture was transferred to a 2 mm electroporation cuvette. Electroporation was performed with a GenePulser Xcell (Bio-Rad Laboratories, München, Germany) at 500 V, 50 µF and 700Ω according to the instructions of the manufacturer. After electroporation the cells were resuspended in 500 µl of stabilization solution and transferred to a culture tube containing 2 ml YPD medium. After regeneration of cells overnight at 30° C. aliquots of the regeneration culture were plated on YPD plates with 0.5 µg cycloheximide per ml. After seven days of incubation at 30° C. several dozen colonies appeared.

EXAMPLE 12

Verification of Presence of Dihydroceramide Desaturase Gene Expression Cassette

Colony PCR was performed to confirm transformation of syringomycinE-resistant *Pichia ciferrii* mutants with plasmid pDB007 carrying the dihydroceramide desaturase gene of *Pichia ciferrii* (DES1) under control of promoter region of the pyruvate dehydrogenase subunit A gene of *Pichia ciferrii* (PDA1).

To that end cells of cycloheximide-resistant colonies from Example 10 were directly used as templates in a PCR using one oligonucleotide binding in the PDA1 promotor region (PDA1-DES1-fw) and the other one in the DES1 gene (PDA1-DES1-rv), yielding a 402 bp fragment only in transformants carrying the DES1 gene under control of the PDA1 promotor:

```
PDA1-DES1-4w:
5'-CTAGGAAAGATAGGGGACAATCAAG-3'    (SEQ ID NO: 29)

PDA1-DES1-rv:
5'-AAGGTTCAGGTCCACAAAGTTCTG-3'     (SEQ ID NO: 30)
```

The presence of the fusion between the *Pichia ciferrii* PDA1 promoter and the *Pichia ciferrii* DES1 could be confirmed by PCR in all cycloheximide-resistant colonies tested.

EXAMPLE 13

Shake Flask Production of Sphingosine-N-Acyl Esters by SyringomycinE Resistant *Pichia ciferrii* Mutants Overexpressing the *Pichia ciferrii* Dihydroceramide Desaturase Gene In order to test for increased production of sphingosine-N-acyl esters by the syringomycinE-resistant mutants overexpressing the *Pichia ciferrii* dihydroceramide desaturase gene one clone of the syringomycinE-resistant mutant carrying vector pDB007 (dihydroceramide desaturase gene expression vector) and the syringomycinE-resistant parent strain were cultivated for shake flask production of sphingosine-N-acyl esters as described in Example 6 for shake flask production of sphinganine by syringomycinE resistant *Pichia ciferrii* mutants, except that 2 µg cycloheximide per ml medium was added in case of the syringomycinE-resistant mutant carrying vector pDB007. Samples were taken after 24 hours (logarithmic growth phase) and 4 days (stationary phase).

10 ml of total fermentation broth were transferred to a 10 ml centrifuge tube, centrifuged 10 min at 5.300×g at 4° C. and the pellet resuspended in 1 ml 0.9% (w/v) sodium chloride containing 10 mg/ml Glucanex (Sigma-Aldrich, Taufkirchen, Germany). The cell suspension was incubated at RT for 1 h, subsequently the cell suspension was sonicated using a Soniprep MSE 3 times for 10 sec with intermittent cooling. The cell suspension was centrifuged 10 min at 5.300×g and the protein concentration in the supernatant determined using a BCA assay according to Smith et. al. (Measurement of protein using bicinchoninic acid. Anal Biochem. 1985 October; 150 (1):76-85) with bovine serum albumin as reference. To 800 µl of the supernatant containing 300 µg protein 3 ml of a chloroform/methanol mixture (1:2 ratio) were added. After vigorously mixing to give one phase the sample was kept at room temperature for one hour. Then the phases were separated by addition of 1 ml chloroform and 1 ml distilled water. After vigorous mixing the sample was centrifuged 13.000×g for 15 min at room temperature. The lower lipid-containing chloroform phase was isolated and evaporated by vacuum centrifugation (Christ Vakuumzentrifuge, Christ AG, Osterode).

EXAMPLE 14

Quantification and Characterization of Sphingosine-N-Acyl Esters by ESI-MS/MS in Dihydroceramide Desaturase Gene Overexpressing SyringomycinE Resistant *Pichia ciferrii* Mutants Sphingosine-N-acyl concentration in cell extracts prepared as described in Example 12 were determined using electrospray ionization tandem mass spectrometry (ESI-MS/MS).

ESI-MS/MS Details

| Instrument: | Quattro Ultima (Micromass) |
|---|---|
| MS | ESI/pos |
| Capillary voltage | 3.5 kV |
| Cone voltage | 50 V |
| RF1 lens voltage | 0.1 V |
| Aperture voltage | 0.0 V |
| RF2 lens voltage | 0.6 V |
| Desolvation temp | 300° C. |
| Source temperature | 100° C. |
| Desolvation gas flow | 660 l per h |
| Cone gas flow | 100 l per h |
| Collision Energy | 25 eV |
| Collision Gas Pressure | $1.0^{-3}$ Torr |
| Ion energy 1 | 0.5 |
| Ion energy 2 | 1.0 |
| Multiplier | 650 V |
| Parent Ion Scanning | m/z 264.2 in the range of m/z 400-800 |

LC Conditions

| Flow | 0.05 ml per min |
|---|---|
| Injection volume | 20 µl full loop |
| Tray temperature | 7° C. |
| Mobile phase | methanol containing 10 mM ammonium formate |

Figure 5:
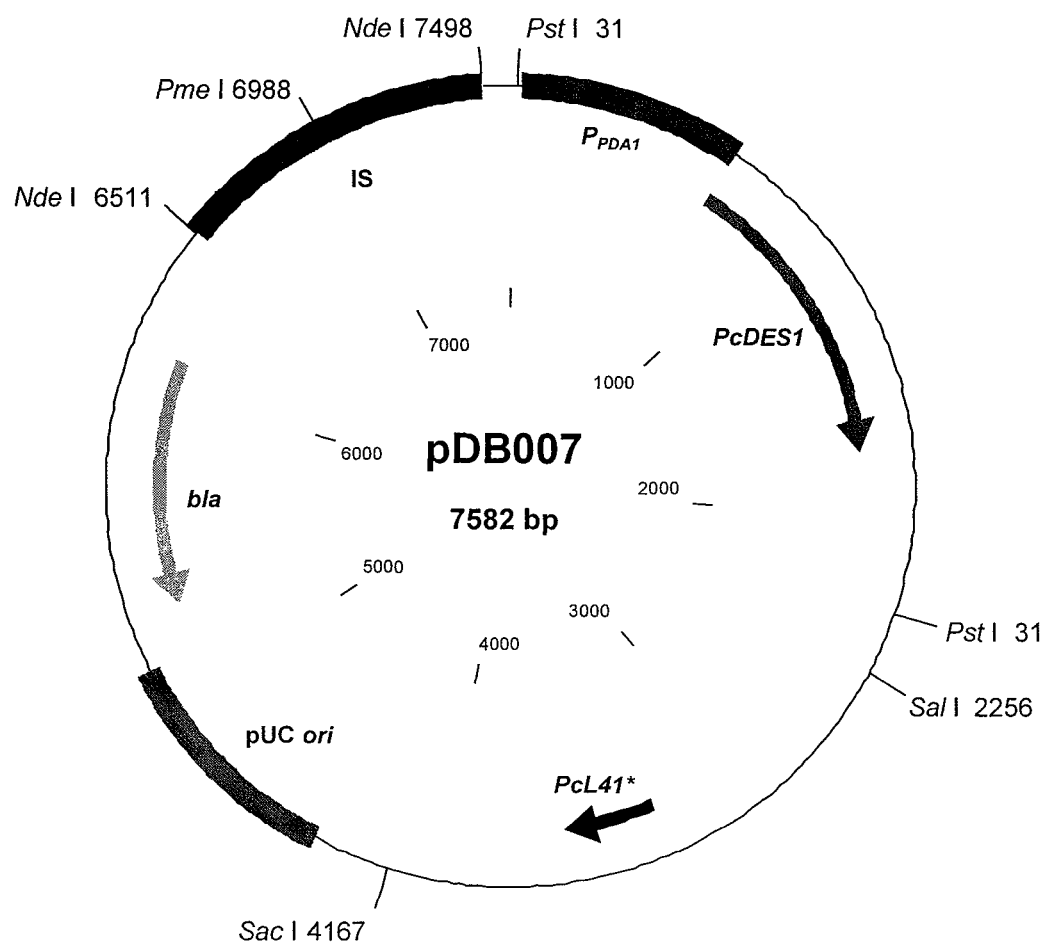
FIG. 5 shows a graphical representation of the plasmid pDB007 for homologous overexpression of DES1 in *Pichia ciferrii*. The PcPDA1 promoter (vertically hatched), the PcDES1 gene (horizontally hatched), the modified PcL41* gene mediating cycloheximide resistance (black), the 5S-26S rDNA intergenic spacer with internal PmeI recognition site (IS; gridded), the ampicillin resistance gene (bla; light grey) and the *E. coli* origin of replication (pUC ori; dark grey) are shown. Restriction sites relevant for the cloning procedures are also indicated.
Figure 6:
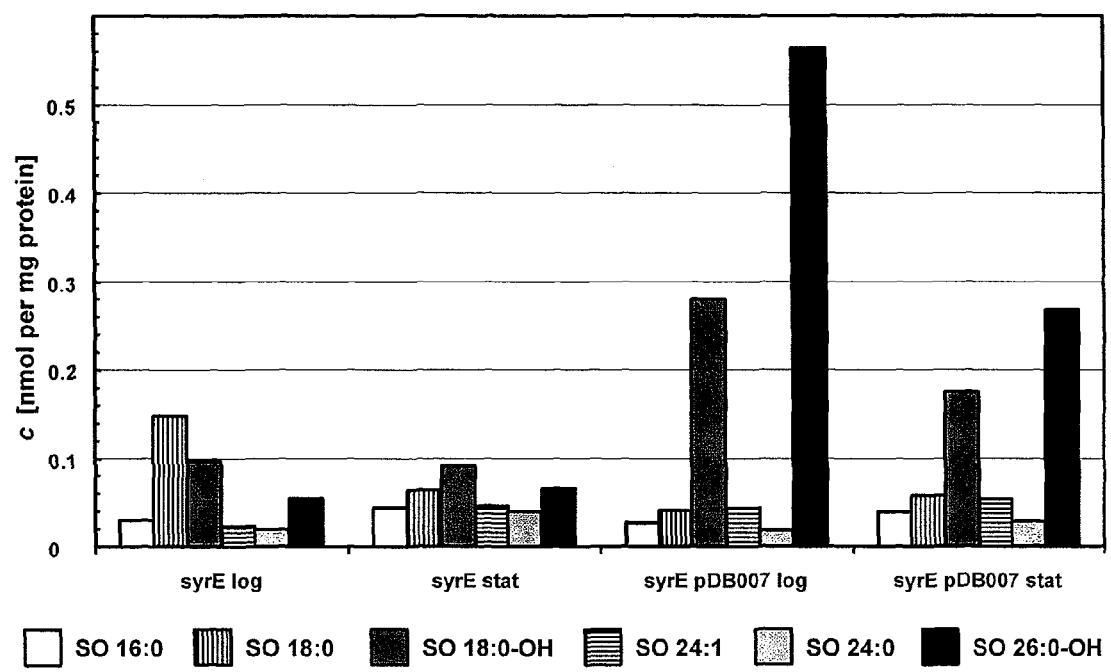
FIG. 6 shows a graphical representation of the quantitation of sphingosine-N-acyl esters in syringomycinE resistant *Pichia ciferrii* mutants with and without PcDES1 overexpression. The absolute concentrations of sphingosine-N-acyl esters with palmitic acid (white), stearic acid (vertically hatched), α-hydroxy stearic acid (dark grey), unsaturated lignoceric acid (horizontally hatched), lignoceric acid (light grey) and α-hydroxy cerotic acid (black) as fatty acid side chain are shown for the following strains: syringomycinE resistant *Pichia ciferrii* mutant with (syrE pDB007) and without PcDES1 overexpression (syrE) in logarithmic growth phase (log; 24 h incubation) and stationary phase (stat; 96 h incubation).

Using that methodology it could be shown that the syringomycinE-resistant mutant overexpressing the *Pichia ciferrii* dihydroceramide desaturase gene produces at least twice as much sphingosine-N-acyl esters as the corresponding parent strain (FIG. 5). The acyl residue was determined to represent almost exclusively α-hydroxy stearic and cerotic acid. N-α-hydroxy-stearoyl-sphingosine was present at 163 ng per mg cellular protein, N-α-hydroxy-cerotyl-sphingosine was present at 392 ng per mg cellular protein. In sum, at least 550 ng sphingosine-N-acyl esters per mg protein were found. As the proportion of protein in total cellular dry weight was determined with 520 mg protein per g cellular dry weight, the total amount of sphingosine-N-acyl esters was 0.29 mg per g cellular dry weight.

The invention claimed is:

1. A method for the production of a mixture of sphingoid bases according to Formula I comprising:
 fermenting a microbial strain of *Pichia ciferrii* under conditions conducive to the production of the sphingoid base; and
 recovering from the fermentation broth at least 0.1 mg per g biomass dry weight of the mixture of sphingoid bases according to Formula I:

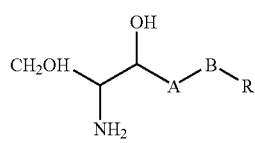

or a salt or ester thereof, wherein:
 A-B is $CH_2$—$CH_2$; and
 R is $(CH_2)_m$—X—$(CH_2)_n$—$CH_3$, where:
  m is 0;
  n is from 8 to 12; and
  X is $CH_2$—$CH_2$, CH=CH, C≡C, or HC=O—$CH_2$;
 wherein the microbial strain of *Pichia ciferrii* is an isolated syringomycinE-resistant subpopulation of cells that produces at least 0.1 mg per g biomass dry weight of the mixture of sphingoid bases base of Formula I.

2. A method for the production of a mixture of sphingoid bases according to Formula I, comprising:
 fermenting a microbial strain of *Pichia ciferrii* under conditions conducive to the production of the sphingoid base; and
 recovering from the fermentation broth at least 10 mg per g biomass dry weight of the mixture of sphingoid bases according to Formula I:

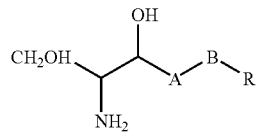

or a salt or ester thereof, wherein:
 A-B is $CH_2$—$CH_2$; and
 R is $(CH_2)_m$—X—$(CH_2)_n$—$CH_3$, where:
  m is 0;
  n is from 8 to 12; and
  X is $CH_2$—$CH_2$, CH=CH, C≡C, or HC=O—$CH_2$;
 wherein the microbial strain of *Pichia ciferrii* is an isolated toxin-resistant subpopulation of cells that produces at least 10 mg per g biomass dry weight of the mixture of sphingoid bases base of Formula I.

3. A method for producing a mixture of sphingoid bases according to Formula I, comprising:
 obtaining a transformed microbial strain of *Pichia ciferrii*, comprising:
  incubating a population of *Pichia ciferrii* cells in a suitable concentration of a toxin,
  selecting a subpopulation of cells that is resistant against the toxin,
  isolating cells out of the toxin-resistant subpopulation of cells that produce at least 0.1 mg per g biomass dry weight of the mixture of sphingoid bases of Formula I, and
  subjecting the isolated toxin-resistant *Pichia ciferrii* cells to DNA-mediated transformation with a polynucleotide encoding dihydroceramide desaturase selected from the group consisting of:
   a polypeptide with the amino acid sequence according to SEQ ID NO:1, and
   a polypeptide with the amino acid sequence having a sequence identity of at least 67% to SEQ ID NO:1;

fermenting the transformed microbial strain under conditions conducive to producing the mixture of sphingoid bases; and
recovering the mixture of sphingoid bases from the fermentation broth;
wherein Formula I is:

$$CH_2OH-\underset{NH_2}{\underset{|}{CH}}-\underset{OH}{\underset{|}{CH}}-A-B-R$$

or an ester or a salt thereof, where:
  A-B is selected from the group consisting of $CH_2$—$CH_2$ and CH=CH; and
  R is $(CH_2)_m$—X—$(CH_2)_n$—$CH_3$, where:
    m is 0;
    n is from 8 to 12; and
    X is $CH_2$—$CH_2$, CH=CH, C≡C, or HC=O—$CH_2$.

4. A method for producing a mixture of sphingoid bases according to Formula I, comprising:
  obtaining a toxin-resistant, transformed microbial strain of *Pichia ciferrii*, comprising:
    subjecting *Pichia ciferrii* cells to DNA-mediated transformation with a polynucleotide encoding dihydroceramide desaturase selected from the group consisting of:
      a polypeptide with the amino acid sequence according to SEQ ID NO:1, and
      a polypeptide with the amino acid sequence having a sequence identity of at least 67% to SEQ ID NO:1,
    incubating the transformed population of *Pichia ciferrii* cells in a suitable concentration of a toxin,
    selecting a subpopulation of cells that is resistant against the toxin, and
    isolating cells out of the toxin-resistant subpopulation of transformed cells that produce at least 0.1 mg per g biomass dry weight of the mixture of sphingoid bases of Formula I, and
  fermenting the isolated toxin-resistant, transformed microbial strain under conditions conducive to producing the mixture of sphingoid bases; and
  recovering the mixture of sphingoid bases from the fermentation broth;
wherein Formula I is:

$$CH_2OH-\underset{NH_2}{\underset{|}{CH}}-\underset{OH}{\underset{|}{CH}}-A-B-R$$

or an ester or a salt thereof, where:
  A-B is selected from the group consisting of $CH_2$—$CH_2$ and CH=CH; and
  R is $(CH_2)_m$—X—$(CH_2)_n$—$CH_3$, where:
    m is 0;
    n is from 8 to 12; and
    X is $CH_2$—$CH_2$, CH=CH, C≡C, or HC=O—$CH_2$.

* * * * *